(12) United States Patent
Kloek et al.

(10) Patent No.: US 7,479,384 B2
(45) Date of Patent: Jan. 20, 2009

(54) NEMATODE MDH-LIKE SEQUENCES

(75) Inventors: Andrew P. Kloek, St. Louis, MO (US);
Brandy Salmon, Durham, NC (US);
Deryck Jeremy Williams, St. Louis, MO (US)

(73) Assignee: Divergence, Inc., St. Louis, MO (US)

( * ) Notice: Subject to any disclaimer, the term of this patent is extended or adjusted under 35 U.S.C. 154(b) by 38 days.

(21) Appl. No.: 10/819,645

(22) Filed: Apr. 6, 2004

(65) Prior Publication Data

US 2004/0237126 A1 Nov. 25, 2004

Related U.S. Application Data

(62) Division of application No. 10/060,848, filed on Jan. 30, 2002, now Pat. No. 6,743,612.

(60) Provisional application No. 60/266,037, filed on Feb. 2, 2001.

(51) Int. Cl.
*C12N 9/04* (2006.01)
*C12N 15/00* (2006.01)
*C12N 1/20* (2006.01)
*C12Q 1/26* (2006.01)
*C12P 21/04* (2006.01)
*A01N 25/00* (2006.01)
*C07H 21/04* (2006.01)
*C12Q 1/00* (2006.01)
*C12Q 1/68* (2006.01)

(52) U.S. Cl. .............................. 435/190; 435/4; 435/6; 435/25; 435/320.1; 435/69.1; 435/71.1; 435/440; 435/252.3; 514/789; 536/23.2

(58) Field of Classification Search .................. 435/190, 435/252.3, 320.1, 69.1, 71.1, 26, 4, 6, 440; 514/789; 536/23.2, 23.7, 23.5; 530/350
See application file for complete search history.

(56) References Cited

OTHER PUBLICATIONS

Guo et al. Proc Natl Acad Sci USA. Jun. 22, 2004;101(25):9205-10.*
GenBank® Accession No. 4021307; GI No. 7275489; McCarter, J.P., Mar. 22, 2000.
GenBank® Accession No. 4313893; GI No. 7921523; McCarter, J.P., May 18, 2000.
GenBank® Accession No. 175534; GI No. 754974; Marra M.A., Mar. 31, 1995.
GenBank® Accession No. 4315085; GI No. 7922734; McCarter, J.P., May 18, 2000.
GenBank® Accession No. 5790215; GI No. 9832327; McCarter, J.P., Aug. 16, 2000.
GenBank® Accession No. T20396; GI No. 7500583; Lennard, N., Jan. 21, 2000.
GenBank® Accession No. T18570; GI No. 7511561; Ainscough, R., Feb. 18, 2000.

Birktoft et al., "Refined Crystal Structure of Cytoplasmic Malate Dehydrogenase at 2.5 Å Resolution" Biochemistry 28:6065-6081, 1989.
Driscoll et al., "NADP+-Dependent Malic Enzyme of Rhizobium meliloti" J. of Bacteriology 178:2224-2231, 1996.
Fahien et al., "Regulation of Malate Dehydrogenase Activity by Glutamate, Citrate, α-Ketoglutarate, and Multienzyme Interaction" J. of Biol. Chem. 263:10687-10697, 1988.
Lai et al., "Mechanism of Activation of the NAD-Malic Enzyme from Ascaris suum by Fumarate" Archives of Biochemistry and Biophys. 299:214-219, 1992.
Landsperger et al., "NAD+-Malic Enzyme" J. of Biol. Chem 251:3599-3602, 1976.
Mitsch et al., "Chimeric Structure of the NAD(P)+-and NADP+-dependent Malic Enzymes of Rhizobium (Sinorhizobium) meliloti" J. of Biol. Chem. 273:9330-9336, 1998.
Prichard et al., "A Comparative Study of the Tricarboxylic Acid Cycle Enzymes in *Fasciola Hepatica* and Rat Liver" Com. Biochem. Physiol. 25:1005-1019, 1968.
Rao et al., "Modification of an Arginine Residue Essential for the Activity of NAD-Malic Enzyme from Ascaris suum" Archives of Biochem. And Biophys. 255:8-13, 1987.
Shonk et al., "Enzyme Patterns in Human Tissues. I. Methods for the Determination of Glycolytic Enzymes" Cancer Res. 24:709-721, 1964.
Spina, Jr. et al., "Purification and Properties of L-Malic Enzyme from *Escherichia coli*" Biochemistry 9:3794-3801, 1970.
GenBank Accession No. AW588457, McCarter, Mar. 22, 2000.
GenBank Accession No. AW827742, McCarter, May 18, 2000.
GenBank Accession No. R05238, Hillier, Mar. 31, 1995.
GenBank Accession No. T18570, Coles, Feb. 18, 2000.
GenBank Accession No. T20396, Lennard, Jan. 21, 2000.
GenBank Accession No. BE581385, McCarter, Aug. 16, 2000.
GenBank Accession No. AW828934, McCarter, May 18, 2000.
Barker et al., "Protein Information Resource: A Community Resource for . . . " Nucl. Acids Res 29(1):29-32, 2001.
Bateman et al., "The Pfam Protein Families Database" Nucl. Acids Res 32(database issue):D138-41, 2004.
Cole et al., GenBank Accession No. F70885, Jun. 20, 2000.
De Azevedo Wash et al., "Transformation of Isopropylamine to L-alaninol . . . " Appl. Environ Microbiol 68(5):2368-75, 2002.
Finn et al., Pfam: clans, web tools and services, Nucl. Acids Res 34 (database issue):D247-51, 2006.
Gayle et al., "Identification of Regions in Interleukin-1 Alpha Important for Activity" J. Biol. Chem 268(29):22105-11, 1993.
Grantham et al., "Glutamine and asparagines synthesis in the nematodes Heligmosomoides . . . " J. Parasitol. 74(6):1052-3, 1988.

(Continued)

*Primary Examiner*—Yong D Pak
(74) *Attorney, Agent, or Firm*—Fish & Richardson P.C.

(57) ABSTRACT

Disclosed are two nucleic acid molecules from *M. incognita* encoding malate dehydrogenase-like (MDH-like) polypeptides. The MDH-like polypeptide sequences are also provided, as are vectors, host cells, and recombinant methods for production of MDH-like nucleotides and polypeptides. The invention further relates to screening methods for identifying inhibitors and/or activators, as well as methods for antibody production.

10 Claims, 4 Drawing Sheets

OTHER PUBLICATIONS

McCarter et al., GenBank Accession No. AW828772, May 10, 2001.
McCarter et al., GenBank Accession No. AW870989, May 10, 2001.
NCBI database Accession No. X60160, Tiboni et al. (Sanangelantoni); Pfam analysis, 1992.
Published Applications Database; U.S. Appl. No. 11/059,867, Kloek et al., Dec. 15, 2005; SEQ ID No. 3, Alignment with SEQ ID No. 2.
Sanangelantoni et al., "The glnA Gene of the Extremely Thermophillic Eubacterium . . . " J. Gen Microbiol. 138(2):383-93, 1992.
Sonnhammer et al., "Pfam: Multiple Sequence Alignments and HMM-profiles . . . " Nucl. Acids. Res 26(1):320-2, 1998.
Whisstock et al., "Prediction of Protein Function from Protein Sequence and Structure" Q Rev Biophys. 36(3):307-40, 2003.

* cited by examiner

```
1
caa gtt tga gat att taa att att att ttg gtg cta aga aaa att ttg tga aaa ATG AAT
                                                                         M   N
61
TAT TCA AAG GAT GCC CCA GAA TTT GTT GTG TCT CCA AAA GAT GCA CGC GAA TTT GTT GTA
 Y   S   K   D   A   P   E   F   V   V   S   P   K   D   A   R   E   F   V   V
121
AAA TGT ATG CAA ACA GTT GGA ACA TCC CCT GAC CAT GCT GGT CAA TTA GCA GAT CTA TTA
 K   C   M   Q   T   V   G   T   S   P   D   H   A   G   Q   L   A   D   L   L
181
TTG GAT GCT GAT CTT GTT GGA CAC TAT AGT CAT GGT CTA AAT CGA CTT CAT ATT TAT GTG
 L   D   A   D   L   V   G   H   Y   S   H   G   L   N   R   L   H   I   Y   V
241
GAT GAC GTC AAA AAC GGA GTT AAA GGA AAT GGA GTT CCA AAA GTG TTA AAA CAA AAA GGA
 D   D   V   K   N   G   V   K   G   N   G   V   P   K   V   L   K   Q   K   G
301
GGC ACT GCT TGG GTT GAT GGA GAA AAT CTT CTG GGT GCA GTT GTT GGA AAC TTC TGT ACC
 G   T   A   W   V   D   G   E   N   L   L   G   A   V   V   G   N   F   C   T
361
GAC TTG GCT ATT AAA TTG GCT AAA GAA TTT GGC GTT GCT TGG GTG GTA ACA AAA AAT TCT
 D   L   A   I   K   L   A   K   E   F   G   V   A   W   V   V   T   K   N   S
421
AAT CAT TAT GGA GCT TGT CAA CAT TAT ACT AAG AAA ATT GCA AAT GCA GGA ATG GTG GGA
 N   H   Y   G   A   C   Q   H   Y   T   K   K   I   A   N   A   G   M   V   G
481
ATG TCT TTT ACA AAT ACA TCG CCT CTC ATG TTC CCC TGC CGA TCT TCT GAG ATT GGA CTT
 M   S   F   T   N   T   S   P   L   M   F   P   C   R   S   S   E   I   G   L
541
GGT ACA AAC CCT CTT TCT TGT TGT GTC AAC TCG GAA AAG ACA GGA GAC AGT TTT TTG TTA
 G   T   N   P   L   S   C   C   V   N   S   E   K   T   G   D   S   F   L   L
601
GAC ATG GCT ACG ACA ACT GTT GCT CTT GGA AAG GTA GAG CTG GCA GAT TGT CGC GGT AAA
 D   M   A   T   T   T   V   A   L   G   K   V   E   L   A   D   C   R   G   K
661
ACA CAA ATT CCC TCC ACA TGG GGT GCC GAT TCT AAA GGC AAT CCA TCG ACT GAT ACA CAA
 T   Q   I   P   S   T   W   G   A   D   S   K   G   N   P   S   T   D   T   Q
721
GTT GTT TTA CAC GGT GGC GGA CTT TTG CCT TTA GGC GGT ATA GAA GAG ACG GGA TCT TAC
 V   V   L   H   G   G   G   L   L   P   L   G   G   I   E   E   T   G   S   Y
781
AAA GGA ACG GGT CTT TCA ATG ATG GGT GAA TTG TTT TGT GGA ATT TTG GCA GGG TCA AGT
 K   G   T   G   L   S   M   M   G   E   L   F   C   G   I   L   A   G   S   S
841
TTT GGA AAA AAT GTA CGA TTA TGG GGG CAA TCA CAC AAA GCC GCT GAC AAT GGC CAA TGT
 F   G   K   N   V   R   L   W   G   Q   S   H   K   A   A   D   N   G   Q   C
901
TTT GTT GCT ATT GAT CAA GAA TGT TTT GCC CCA GGA TTT GCT CCT CGT TTA CAA CAA TTT
 F   V   A   I   D   Q   E   C   F   A   P   G   F   A   P   R   L   Q   Q   F
961
TTG GAT GAA ACA CGG AAT TTG AAA CCG ATT TCT GAA GAA AAG CCT GTT CTA GTG CCT GGA
 L   D   E   T   R   N   L   K   P   I   S   E   E   K   P   V   L   V   P   G
1021
GAT CCT GAA AGA ATG AAT ACA GAA TAT AGC CAA AAG GCT GGA GGT TTG GTA TAC CAA GAA
 D   P   E   R   M   N   T   E   Y   S   Q   K   A   G   G   L   V   Y   Q   E
1081
GGG CAG ATA AAA GCT TTG GAA GAG TTG GCC ACA AAA TGT GAT GTT CAA ATG TTC TCA TAC
 G   Q   I   K   A   L   E   E   L   A   T   K   C   D   V   Q   M   F   S   Y
1141
AAA CGA CTA AAA tga gga tga gat tta aat att ttt ttg tgt agc tga aac tga ctt caa
 K   R   L   K   *
1201
acg aga aat gaa caa ttt cct aaa aag cag tta gat aag ggt tta ttt ttc att tat tta 1261
ttt ttt aac ctc att ttt tat ata cga ata aaa tta atg ctc *aa aaa aaa aaa aaa aaa 1321
aaa aaa a
```

FIG. 1

```
1
tgg tgc taa gaa aaa ttt tgt gcg aaa ATG AAT TAT TCA AAG GAT GCC CCA GAA TTT GTT
                                    M   N   Y   S   K   D   A   P   E   F   V
61
GTC TCT CCA AAA GAT GCT CGC GAA TTT GTT GTA AAA TGT ATG CAA ACA GTT GGA ACA TCC
V   S   P   K   D   A   R   E   F   V   V   K   C   M   Q   T   V   G   T   S
121
CCT GAC CAT GCT GGT CAA TTA GCA GAT CTC TTA TTA GAT GCT GAT CTT GTT GGG CAT TAC
P   D   H   A   G   Q   L   A   D   L   L   L   D   A   D   L   V   G   H   Y
181
AGT CAT GGT CTA AAT CGG CTT CAT ATT TAT GTG GAT GAC GTC AAA AAT GGA GTT AAA GGA
S   H   G   L   N   R   L   H   I   Y   V   D   D   V   K   N   G   V   K   G
241
AAT GGA GTT CCA AAA GTG TTA AAA CAA AAA GGA GGC ACT GCT TGG GTG GAT GGA GAA AAT
N   G   V   P   K   V   L   K   Q   K   G   G   T   A   W   V   D   G   E   N
301
CTT TTG GGT GCA GTT GTT GGC AAC TTC TGT ACC GAT TTG GCT ATT AAA TTG GCT AAA GAA
L   L   G   A   V   V   G   N   F   C   T   D   L   A   I   K   L   A   K   E
361
TTT GGT GTT GCT TGG GTG GTA ACA AAA AAT TCT AAT CAT TAT GGA GCT *GT CAA CAT TAT
F   G   V   A   W   V   V   T   K   N   S   N   H   Y   G   A   X   Q   H   Y
421
ACT AAG AAA ATT GCG AAT GCA GGA ATG GTG GGA ATG TCA TTT ACA AAT ACT TCA CCT CTC
T   K   K   I   A   N   A   G   M   V   G   M   S   F   T   N   T   S   P   L
481
ATG TTC CCC TGC CGT TCT TCT GAG ATC GGA CTA GGC ACA AAC CCT CTT TCT TGT TGT GCC
M   F   P   C   R   S   S   E   I   G   L   G   T   N   P   L   S   C   C   A
541
AAC TCG GAA AAG ACA GAA GAC AGT TTT TTG TTA GAC ATG GCT ACT ACA ACT GTT GCT CTA
N   S   E   K   T   E   D   S   F   L   L   D   M   A   T   T   T   V   A   L
601
GGA AAG GTT GAG CTG GCA AAT TGT CGC GGT AAA ACA CAA ATT CCC TCA GCA TGG GGT GCC
G   K   V   E   L   A   N   C   R   G   K   T   Q   I   P   S   A   W   G   A
661
GAT TCT AAA GGC AAT CCA TCA ACA GAC ACA CAA GTT GTT TTA CAT GGT GGC GGA CTT TTG
D   S   K   G   N   P   S   T   D   T   Q   V   V   L   H   G   G   G   L   L
721
CCT TTA GGC GGT ATA GAA GAG ACG GGA TCT TAC AAA GGA ACG GGT CTC TCA ATG ATG GGT
P   L   G   G   I   E   E   T   G   S   Y   K   G   T   G   L   S   M   M   G
781
GAA TTG TTT TGT GGA ATT TTG GCA GGG TCA AGT TTT GGA AAA AAT GTA CGA TTA TGG GGG
E   L   F   C   G   I   L   A   G   S   S   F   G   K   N   V   R   L   W   G
841
CAA TCA CAC AAA GCC GCT GAC AAT GGC CAA TGT TTT GTT GCT ATT GAT CAA GAA TGT TTT
Q   S   H   K   A   A   D   N   G   Q   C   F   V   A   I   D   Q   E   C   F
901
GCC CCA GGA TTT GCT CCT CGT TTA CAA CAA TTT TTG GAT GAA ACA CGG AAT TTG AAA CCG
A   P   G   F   A   P   R   L   Q   Q   F   L   D   E   T   R   N   L   K   P
961
ATT TCT GAA GAA AAG CCT GTT CTA GTG CCT GGA GAT CCT GAA AGA ATG AAT ACA GAA TAT
I   S   E   E   K   P   V   L   V   P   G   D   P   E   R   M   N   T   E   Y
1021
AGC CAA AAG GCT GGA GGT TTG GTA TAC CAA GAA GGG CAG ATA AAA GCT TTG GAA GAG TTG
S   Q   K   A   G   G   L   V   Y   Q   E   G   Q   I   K   A   L   E   E   L
1081
GCC ACA AAA TGT GAT GTT CAA ATG TTC TCA TAC AAA CGA CTA AAA TGA gga tga gat tta
A   T   K   C   D   V   Q   M   F   S   Y   K   R   L   K   *
1141
aat att ttt ttg tgt agc tga aac tga ctt caa acg aga aat gaa caa ttt cct aaa aag 1201
cag tta gat aag ggt tta ttt ttc att tat tta ttt ttt aac ctc att ttt tat ata cga 1261
agc aga tat gac tga aac tgg agg tgg tga ttc tgt tga atc tgc aag tgt tta tgc taa
```

FIG. 2A

```
1321
ctc tgt ttg tga aat gtg cgg aaa tta tga ggt tca act tca aac aat tca aag cag tca 1381
gga tac tct cag gga gaa att ggc agc tgc taa aga att gta tga gaa ata tgg caa gga 1441
att gac aga aga gag gca tta tcg aaa gga att gga aat taa att tgc tgc ttt aaa tga 1501
aga aac tga agg gaa aat tca gca atg tat tac caa tac aga aga ctt tga cag cgt att 1561
gcc ttc tca gta aaa aac aa* aag ctg att tgt ctg ttt tgg aat c*c aat tag aat tgg 1621
cta gga atc gtc aaa aag agc ttc aag aac aat tgg ttt tgt taa atg aaa ggt atg aaa 1681
aac ttt tac att taa aat ctc aat gtg ctg aag aaa tgc gtg aac aac aaa ttg aac tgc 1721
ctc aaa cag ttg aag aac ttc aat ttt tgg cat tgc agt tga *ag agg aat tga taa ctg 1781
aac gtg cag cac gtg agc atg aaa gga ggg aat taa atg atg aat tgg cta tgg cac gtc 1841
aac agc ttg ttg aat tgg aaa ttt gtc c*a gag aaa atg aag aat gaa ttt tat gat ata 1901
taa aaa tat att tat ttt gct caa ata g*t ttt ata aat ttt aag agc tga tag aaa aat 1961
tta gtt ttg *aa ttt ttg aag aat ata ttt t*t acg gtt tgc ac* cct tag aat ggt ttt 2021
gtt tta ata aat gc* c*g gtt gg* aaa aaa aaa aaa aaa aaa aaa aaa
```

FIG. 2B

Amino acid alignment

1 *M. incognita* MDH1
2 *M. incognita* MDH2
3 *C. elegans* MDH1
4 *C. elegans* MDH2

```
         . . . .10. . . . .20. . . . .30. . . . .40. . . . .50. . . . .60
1  ..............................MNYS.....KDAPEFVVSPKDAREFVVK: 23
2  ..............................MNYS.....KDAPEFVVSPKDAREFVVK: 23
3  ..........................MTIKDKREFNETDEIVISKEKLDSFVLE: 28
4  MNLLQRALVFTGGHISRYQAVIAVNSVGKNARFYSTTDDNMAAPEESVVAKDEMKRFMVE: 60

. . . .70. . . . .80. . . . .90. . . .100. . . .110. . . .120
1  CMQTVGTSPDHAGQLADLLLDADLVGHYSHGLNRLHIYVDDVKNG.VKGNGVPKVLKQKG: 82
2  CMQTVGTSPDHAGQLADLLLDADLVGHYSHGLNRLHIYVDDVKNG.VKGNGVPKVLKQKG: 82
3  CLAKAGCTGDHAQQLAETLLCSDYRGHYSHGINRLHIYVHDLMMKSTAVTGTPQVLKSKG: 88
4  CMTKVGATESHATQLALVLLEGDIRGHYSHGLNRLDMYVRDIEQNVCKGDGEPIILKEKA:120

. . .130. . . .140. . . .150. . . .160. . . .170. . . .180
1  GTAWVDGENLLGAVVGNFCTDLAIKLAKEFGVAWVVTKNSNHYGACQHYTKKIANAGMVG:142
2  GTAWVDGENLLGAVVGNFCTDLAIKLAKEFGVAWVVTKNSNHYGACQHYTKKIANAGMVG:142
3  STAWVDGNNLLGPVVGNFCMQLAVEKAKEFGIGWVVCRNSNHFGIAGWYADFACRNGLVG:148
4  GTAWVDGENLLGPVVGNFCMDLAIEKAKNACIGWVVAKGSNHYGIAGWYALRAMKKGMLG:180

. . .190. . . .200. . . .210. . . .220. . . .230. . . .240
1  MSFTNTSPLMFPCRSSEIGLGTNPLSCCVNSEKTGDSFLLDMATTTVALGKVELADCRGK:202
2  MSFTNTSPLMFPCRSSEIGLGTNPLSCCANSEKTEDSFLLDMATTTVALGKVELANCRGK:202
3  MAFTNTSPCVFPTGSREKSLGSNPI.CMAAPGMEGDSFIDMASTTVAYGKIEVVDRKGE:207
4  MSMTNTSPISFPTRSAVPALGTNPI.SLAAPGTGDDSFVLDMASTTVAIGKVELAARK.E:238

. . .250. . . .260. . . .270. . . .280. . . .290. . . .300
1  TQIPSTWGADSKGNPSTDTQVVLEGGGLLPLGGIEETGSYKGTGLSMMGELFCGILAGSS:262
2  TQIPSAWGADSKGNPSTDTQVVLEGGGLLPLGGIEETGSYKGTGLSMMGELFCGILAGSS:262
3  TYIPGSWGADKNGDETHNPKEVLDGGGLQPLGGSEITGGYKGTGLCMMVEVLCGIMGGSA:267
4  NPVPLSWGVGEGGKETTDPTKVLYGGGLLPLGGVEVSGGYKGYGLSSMIEIFCGILAGAH:298

. . .310. . . .320. . . .330. . . .340. . . .350. . . .360
1  FGKNVRLWGQSHKAADNGQCFVAIDQECFAPGFAPRLQQFLDETRNLKPISEEKPVLVPG:322
2  FGKNVRLWGQSHKAADNGQCFVAIDQECFAPGFAPRLQQFLDETRNLKPISEEKPVLVPG:322
3  FGKNIRQWQTTSKTADLGQCFVAIDPECFAPGFSNRLQEFCDETRNLNPINPSRPPQVPG:327
4  WGPHVRKWMSTKSEADLGQCFVAIDPEAFAPGFADRLQDNMQTMRALPTSSPSFKVEVAG:358

. . .370. . . .380. . . .390. . . .400. . .
1  DPERMNTEYSQKAGGLVYQEGQIKALEELATKCDVQMFSYKRLK..:366
2  DPERMNTEYSQKAGGLVYQEGQIKALEELATKCDVQMFSYKRLK..:366
3  DPERAHMNMCDDLGGIVYKKKQLDHIKNLADRLGVILRLVDEKPQ:372
4  DMERRHEALVEQLGGIPYHKNQITFVNDLAAKLGVKTVDLVQ...:400
```

NEMATODE MDH-LIKE SEQUENCES

CROSS-REFERENCE TO RELATED APPLICATIONS

This application is a divisional of U.S. application Ser. No. 10/060,848, filed Jan. 30, 2002, now U.S. Pat. No. 6,743,612 which claims priority to provisional application Ser. No. 60/266,037, filed Feb. 2, 2001, the contents of which are hereby incorporated by reference.

BACKGROUND

Nematodes (derived from the Greek word for thread) are active, flexible, elongate, organisms that live on moist surfaces or in liquid environments, including films of water within soil and moist tissues within other organisms. While only 20,000 species of nematode have been identified, it is estimated that 40,000 to 10 million actually exist. Some species of nematodes have evolved as very successful parasites of both plants and animals and are responsible for significant economic losses in agriculture and livestock and for morbidity and mortality in humans (Whitehead (1998) *Plant Nematode Control*. CAB International, New York).

Nematode parasites of plants can inhabit all parts-of plants, including roots, developing flower buds, leaves, and stems. Plant parasites are classified on the basis of their feeding habits into the broad categories: migratory ectoparasites, migratory endoparasites, and sedentary endoparasites. Sedentary endoparasites, which include the root knot nematodes (*Meloidogyne*) and cyst nematodes (*Globodera* and *Heterodera*) induce-feeding sites and establish long-term infections within roots that are often very damaging to crops (Whitehead, supra). It is estimated that parasitic nematodes cost the horticulture and agriculture industries in excess of $78 billion worldwide a year, based on an estimated average 12% annual loss spread across all major crops. For example, it is estimated that nematodes cause soybean losses of approximately $3.2 billion annually worldwide (Barker et al. (1994) *Plant and Soil Nematodes: Societal Impact and Focus for the Future*. The Committee on National Needs and Priorities in Nematology. Cooperative State Research Service, US Department of Agriculture and Society of Nematologists). Several factors make the need for safe and effective nematode controls urgent. Continuing population growth, famines, and environmental degradation have heightened concern for the sustainability of agriculture, and new government regulations may prevent or severely restrict the use of many available agricultural anthelmintic agents.

The situation is particularly dire for high value crops such as strawberries and tomatoes where chemicals have been used extensively to control soil pests. The soil fumigant methyl bromide has been used effectively to reduce nematode infestations in a variety of these specialty crops. It is however regulated under the U.N. Montreal Protocol as an ozone-depleting substance and is scheduled for elimination in 2005 in the US (Carter (2001) *Califonia Agriculture*, 55(3):2). It is expected that strawberry and other commodity crop industries will be significantly impacted if a suitable replacement for methyl bromide is not found. Presently there are a very small array of chemicals available to control nematodes and they are frequently inadequate, unsuitable, or too costly for some crops or soils (Becker (1999) *Agricultural Research Magazine* 47(3):22-24; U.S. Pat. Nos. 6,048,714). The few available broad-spectrum nematicides such as Telone (a mixture of 1,3-dichloropropene and chloropicrin) have significant restrictions on their use because of toxicological concerns (Carter (2001) *California Agriculture*, Vol. 55(3):12-18).

Fatty acids are a class of natural compounds that have been investigated as alternatives to the toxic, non-specific organophosphate, carbamate and fumigant pesticides (Stadler et al. (1994) *Planta Medica* 60(2): 128-132; U.S. Pat. Nos. 5,192,546; 5,346,698; 5,674,897; 5,698,592; 6,124,359). It has been suggested that fatty acids derive their pesticidal effects by adversely interfering with the nematode cuticle or hypodermis via a detergent (solubilization) effect, or through direct interaction of the fatty acids and the lipophilic regions of target plasma membranes (Davis et al. (1997) *Journal of Nematology* 29(4S):677-684). In view of this general mode of action it is not surprising that fatty acids are used in a variety of pesticidal applications including as herbicides (e.g., SCYTHE by Dow Agrosciences is the C9 saturated fatty acid pelargonic acid), as bactericides and fungicides (U.S. Pat. Nos. 4,771,571; 5,246,716) and as insecticides (e.g., SAFER INSECTICIDAL SOAP by Safer, Inc.).

The phytotoxicity of fatty acids has been a major constraint on their general use in agricultural applications (U.S. Pat. No. 5,093,124) and the mitigation of these undesirable effects while preserving pesticidal activity is a major area of research. The esterification of fatty acids can significantly decrease their phytotoxicity (U.S. Pat. Nos. 5,674,897; 5,698,592; 6,124,359). Such modifications can however lead to dramatic loss of nematicidal activity as is seen for linoleic, linolenic and oleic acid (Stadler et al. (1994) *Planta Medica* 60(2):128-132) and it may be impossible to completely decouple the phytotoxicity and nematicidal activity of pesticidal fatty acids because of their non-specific mode of action. Perhaps not surprisingly, the nematicidal fatty acid pelargonic acid methyl ester (U.S. Pat. Nos. 5,674,897; 5,698,592; 6,124,359) shows a relatively small "therapeutic window" between the onset of pesticidal activity and the observation of significant phytotoxicity (Davis et al. (1997) *J Nematol* 29(4S):677-684). This is the expected result if both the phytotoxicity and the nematicidial activity derive from the non-specific disruption of plasma membrane integrity. Similarly the rapid onset of pesticidal activity seen with many nematicidal fatty acids at therapeutic concentrations (U.S. Pat. Nos. 5,674,897; 5,698,592; 6,124,359) suggests a non-specific mechanism of action, possibly related to the disruption of membranes, action potentials and neuronal activity.

Ricinoleic acid, the major component of castor oil, provides another example of the unexpected effects esterification can have on fatty acid activity. Ricinoleic acid has been shown to have an inhibitory effect on water and electrolyte absorption using everted hamster jejunal and ileal segments (Gaginella et al. (1975) *J Pharmacol Exp Ther* 195(2):355-61) and to be cytotoxic to isolated intestinal epithelial cells (Gaginella et al. (1977) *J Pharmacol Exp Ther* 201(1):259-66). These features are likely the source of the laxative properties of castor oil which is given as a purgative in humans and livestock. In contrast, the methyl ester of ricinoleic acid is ineffective at suppressing water absorption in the hamster model (Gaginella et al. (1975) *J Pharmacol Exp Ther* 195(2): 355-61). (N.B. Castor oil is a component of some de-worming protocols because of its laxative properties.)

The macrocyclic lactones (e.g., avermectins and milbemycins) and delta-toxins from *Bacillus thuringiensis* (Bt) are chemicals that in principle provide excellent specificity and efficacy and should allow environmentally safe control of plant parasitic nematodes. Unfortunately, in practice, these two approaches have proven less effective for agricultural applications against root pathogens. Although certain avermectins show exquisite activity against plant parasitic nematodes these chemicals are hampered by poor bioavailability due to their light sensitivity, degradation by soil microorganisms and tight binding to soil particles (Lasota & Dybas (1990) *Acta Leiden* 59(1-2):217-225; Wright & Perry (1998) Musculature and Neurobiology. In: The Physiology and Biochemistry of Free-Living and Plant-parasitic Nematodes (eds R. N. Perry & D. J. Wright), CAB International 1998). Consequently despite years of research and extensive use against animal parasitic nematodes, mites and insects (plant and animal applications), macrocyclic lactones (e.g., avermectins and milbemycins) have never been commercially developed to control plant parasitic nematodes in the soil.

Bt delta toxins must be ingested to affect their target organ the brush border of midgut epithelial cells (Marroquin et al. (2000) *Genetics*. 155(4):1693-1699). Consequently they are not anticipated to be effective against the dispersal, non-feeding, juvenile stages of plant parasitic nematodes in the field. These juvenile stages only commence feeding when a susceptible host has been infected, thus to be effective nematicides may need to penetrate the cuticle. In addition, soil mobility of a relatively large 65-130 kDa protein—the size of typical: Bt delta toxins—is expected to be poor and delivery in planta is likely to be constrained by the exclusion of large particles by the feeding tube of certain plant parasitic nematodes such as *Heterodera* (Atkinson et al. (1998) Engineering resistance to plant-parasitic nematodes. In: The Physiology and Biochemistry of Free-Living and Plant-parasitic Nematodes (eds R. N. Perry & D. J. Wright), CAB International 1998).

Many plant species are known to be highly resistant to nematodes. The most well documented of these include marigolds (*Tagetes* spp.), rattlebox (*Crotalaria spectabilis*), chrysanthemums (*Chrysanthemum* spp.), castor bean (*Ricinus communis*), margosa (*Azardiracta indica*), and many members of the family *Asteraceae* (family *Compositae*) (Hackney & Dickerson. (1975) *J Nematol* 7(1):84-90). The active principle(s) for this nematicidal activity has not been discovered in all of these examples and no plant-derived products are sold commercially for control of nematodes. In the case of the *Asteraceae,* the photodynamic compound alpha-terthienyl has been shown to account for the strong nematicidal activity of the roots. Castor beans are plowed under as a green manure before a seed crop is set. However, a significant drawback of the castor plant is that the seed contains toxic compounds (such as ricin) that can kill humans, pets, and livestock and is also highly allergenic.

There remains an urgent need to develop environmentally safe, target-specific ways of controlling plant parasitic nematodes. In the specialty crop markets, economic hardship resulting from nematode infestation is highest in strawberries, bananas, and other high value vegetables and fruits. In the high-acreage crop markets, nematode damage is greatest in soybeans and cotton. There are however, dozens of additional crops that suffer from nematode infestation including potato, pepper, onion, citrus, coffee, sugarcane, greenhouse ornamentals and golf course turf grasses.

Nematode parasites of vertebrates (e.g., humans, livestock and companion animals) include gut roundworms, hookworms, pinworms, whipworms, and filarial worms. They can be transmitted in a variety of ways, including by water contamination, skin penetration, biting insects, or by ingestion of contaminated food.

In domesticated animals, nematode control or "de-worming" is essential to the economic viability of livestock producers and is a necessary part of veterinary care of companion animals. Parasitic nematodes cause mortality in animals (e.g., heartworm in dogs and cats) and morbidity as a result of the parasites' inhibiting the ability of the infected animal to absorb nutrients. The parasite-induced nutrient deficiency results in diseased livestock and companion animals (i.e., pets), as well as in stunted growth. For instance, in cattle and dairy herds, a single untreated infection with the brown stomach worm can permanently stunt an animal's ability to effectively convert feed into muscle mass or milk.

Two factors contribute to the need for novel anthelmintics and vaccines for control of parasitic nematodes of animals. First, some of the more prevalent species of parasitic nematodes of livestock are building resistance to the anthelmintic drugs available currently, meaning that these products will eventually lose their efficacy. These developments are not surprising because few effective anthelmintic drugs are available and most have been used continuously. Presently a number of parasitic species has developed resistance to most of the anthelmintics (Geents et al. (1997) Parasitology Today 13:149-151; Prichard (1994) Veterinary Parasitology 54:259-268). The fact that many of the anthelmintic drugs have similar modes of action complicates matters, as the loss of sensitivity of the parasite to one drug is often accompanied by side resistance—that is, resistance to other drugs in the same class (Sangster & Gill (1999) Parasitology Today Vol. 15(4):141-146). Secondly, there are some issues with toxicity for the major compounds currently available.

Human infections by nematodes result in significant mortality and morbidity, especially in tropical regions of Africa, Asia, and the Americas. The World Health Organization estimates 2.9 billion people are infected with parasitic nematodes. While mortality is rare in proportion to total infections (180,000 deaths annually), morbidity is tremendous and rivals tuberculosis and malaria in disability adjusted life year measurements. Examples of human parasitic nematodes include bookworm, filarial worms, and pinworms. Hookworm is the major cause of anemia in millions of children, resulting in growth retardation and impaired cognitive development. Filarial worm species invade the lymphatics, resulting in permanently swollen and deformed limbs (elephantiasis) and invade the eyes causing African Riverblindness. *Ascaris lumbricoides,* the large gut roundworm infects more than one billion people worldwide and causes malnutrition and obstructive bowl disease. In developed countries, pinworms are common and often transmitted through children in daycare.

Even in asymptomatic parasitic infections, nematodes can still deprive the host of valuable nutrients and increase the ability of other organisms to establish secondary infections. In some cases, infections can cause debilitating illnesses and can result in anemia, diarrhea, dehydration, loss of appetite, or death.

While public health measures have nearly eliminated one tropical nematode (the water-borne Guinea worm), cases of other worm infections have actually increased in recent decades. In these cases, drug intervention provided through foreign donations or purchased by those who can afford it remains the major means of control. Because of the high rates of reinfection after drug therapy, vaccines remain the best hope for worm control in humans. There are currently no vaccines available.

Until safe and effective vaccines are discovered to prevent parasitic nematode infections, anthelmintic drugs will continue to be used to control and treat nematode parasitic infections in both humans and domestic animals. Finding effective compounds against parasitic nematodes has been complicated by the fact that the parasites have not been amenable to culturing in the laboratory. Parasitic nematodes are often obligate parasites (i.e., they can only survive in their respective hosts, such as in plants, animals, and/or humans) with slow generation times. Thus, they are difficult to grow under artificial conditions, making genetic and molecular experimentation difficult-or impossible. To circumvent these limitations, scientists have used *Caenorhabidits elegans* as a model system for parasitic nematode discovery efforts.

*C. elegans* is a small free-living bacteriovorous nematode that for many years has served as an important model system for multicellular animals (Burglin (1998) *Int. J. Parasitol.,* 28(3): 395-411). The genome of *C. elegans* has been completely sequenced and the nematode shares many general developmental and basic cellular processes with vertebrates (Ruvkin et al. (1998) *Science* 282: 2033-41). This, together with its short generation time and ease of culturing, has made it a model system of choice for higher eukaryotes (Aboobaker et al. (2000) *Ann. Med.* 32: 23-30).

Although *C. elegans* serves as a good model system for vertebrates, it is an even better model for study of parasitic nematodes, as *C. elegans* and other nematodes share unique biological processes not found in vertebrates. For example, unlike vertebrates, nematodes produce and use chitin, have gap junctions comprised of innexin rather than connexin and contain glutamate-gated chloride channels rather than glycine-gated chloride channels (Bargmann (1998) *Science* 282: 2028-33). The latter property is of particular relevance given that the avermectin class of drugs is thought to act at glutamate-gated chloride receptors and is highly selective for invertebrates (Martin (1997) *Vet. J.* 154:11-34).

A subset of the genes involved in nematode specific processes will be conserved in nematodes and absent or significantly diverged from homologues in other phyla. In other words, it is expected that at least some of the genes associated with functions unique to nematodes will have restricted phylogenetic distributions. The completion of the *C. elegans* genome project and the growing database of expressed sequence tags (ESTs) from numerous nematodes facilitate identification of these "nematode specific" genes. In addition, conserved genes involved in nematode-specific processes are expected to retain the same or very similar functions in different nematodes. This functional equivalence has been demonstrated in some cases by transforming *C. elegans* with homologous genes from other nematodes (Kwa et al. (1995) *J. Mol. Biol.* 246:500-1 0; Redmond et al. (2001) *Mol. Biochem. Parasitol.* 112:125-131). This sort of data transfer has been shown in cross phyla comparisons for conserved genes and is expected to be more robust among species within a phylum. Consequently, *C. elegans* and other free-living nematode species are likely excellent surrogates for parasitic nematodes with respect to conserved nematode processes.

Many expressed genes in *C. elegans* and certain genes in other free-living nematodes can be "knocked out" genetically by a process referred to as RNA interference (RNAi), a technique that provides a powerful experimental tool for the study of gene function in nematodes (Fire et al. (1998) *Nature* 391(6669):806-81 1; Montgomery et al. (1998) *Proc. Natl. Acad Sci USA* 95(26):15502-15507). Treatment of a nematode with double-stranded RNA of a selected gene can destroy expressed sequences corresponding to the selected gene thus reducing expression of the corresponding protein. By preventing the translation of specific proteins, their functional significance and essentiality to the nematode can be assessed. Determination of essential genes and their corresponding proteins using *C. elegans* as a model system will assist in the rational design of anti-parasitic nematode control products.

SUMMARY

The invention features nucleic acid molecules encoding *M. incognita* malate dehydrogenase (MDH) and other nematode MDH-like polypeptides. *M. incognita* is a root knot nematode that causes substantial damage to crops, particularly to cotton, tobacco, pepper, and tomato. In part, the MDH-like nucleic acids and polypeptides of the invention allow for the identification of a nematode species, and for the identification of compounds that bind or alter the activity of MDH-like polypeptides. Such compounds may provide a means of combating diseases and infestations caused by nematodes, particularly by *M. incognita*, e.g., in tobacco, cotton, pepper or tomato plants.

The invention is based, in part, on the identification of a cDNA (complimentary DNA) encoding *M. incognita* MDH I (SEQ ID NO:1). This 1327 nucleotide cDNA has a 1098 nucleotide open reading frame (SEQ ID NO:5) encoding a 366 amino acid polypeptide (SEQ ID NO:3). The invention is also based, in part, on the identification of a cDNA encoding *M. incognita* MDH2 (SEQ ID NO:2). This 2068 nucleotide cDNA has a 1098 nucleotide open reading frame (SEQ ID NO:6) encoding a 366 amino acid polypeptide (SEQ ID NO:4).

In one aspect, the invention features novel nematode malate dehydrogenase (MDH)-like polypeptides. Such polypeptides include purified polypeptides having the amino acid sequences set forth in SEQ ID NO:3 and SEQ ID NO:4. Also included are polypeptides having an amino acid sequence that is at least about 60%, 70%, 75%, 80%, 85%, 90%, 95%, or 98% identical to SEQ ID NO:3 and/or 4. The purified polypeptides can be encoded by a nematode gene, e.g., a nematode other than *C. elegans*. For example, the purified polypeptide have a sequence other than SEQ ID NO:7 or 8 (*C. elegans* MDH1 and MDH2 respectively). The purified polypeptides can further include a heterologous amino acid sequence, e.g., an amino-terminal or carboxy-terminal sequence derived from a different polypeptide. Also featured are purified polypeptide fragments of the aforementioned MDH-like polypeptides, e.g., a fragment comprising at least about 40, 50, 75, 100, 150, 189, 191, 200, 250, 300, or 355 amino acids of SEQ ID NO:3; SEQ ID NO:4, or the amino acid sequence of some other MDH-like polypeptide other than *C. elegans* MDH1 or MDH2. Non-limiting examples of such fragments include: fragments comprising about amino acid 1 to 149, 1 to 200, 1 to 223, 100 to 223, 149 to 223, 149 to 336, 200 to 366, and 223 to 366 of SEQ ID NO:3 and 4. The polypeptide or fragment thereof can be modified, e.g., processed, truncated, modified (e.g. by glycosylation, phosphorylation, acetylation, myristylation, prenylation, palmitoylation, amidation, addition of glycerophosphatidyl inositol), or any combination of the above. Also within the invention are polypeptides consisting of or consisting essentially of such fragments.

Certain MDH-like polypeptides comprise a sequence of 371 amino acids or fewer.

In another aspect, the invention features novel isolated nucleic acid molecules encoding a nematode MDH-like polypeptide. Such isolated nucleic acid molecules include nucleic acids having the nucleotide sequence set forth in SEQ ID NO:1, SEQ ID NO:2, SEQ ID NO:5, or SEQ ID NO:6. Also included are isolated nucleic acid molecules having the same sequence as or encoding the same polypeptide as a nematode MDH-like gene (other than the *C. elegans* MDH-like genes, MDH1 and MDH2).

Also featured are: 1) isolated nucleic acid molecules having a strand that hybridizes under low stringency conditions to a single stranded probe of the sequence of SEQ ID NO:1 or 2 or their complements and, optionally, encodes a polypeptide of between 280 and 372 amino acids; 2) isolated nucleic acid molecules having a strand that hybridizes under high stringency conditions to a single stranded probe of the sequence of SEQ ID NO:1 or 2 or their complements and, optionally, encodes a polypeptide of between 280 and 372 amino acids; 3) isolated nucleic acid fragments of MDH-like nucleic acid molecule, e.g., a fragment of SEQ ID NO:1 that is about 573, 575, 750, 1000, 1300, 1500, 1750, or more nucleotides in length or ranges between such lengths, or a fragment of SEQ ID NO:2 that is about 567, 575, 600, 750, 1000, 1300, 1500, 1750, or more nucleotides in length or ranges between such lengths; and 4) oligonucleotides that are complementary to an MDH-like nucleic acid molecule or an MDH-like nucleic acid complement, e.g., an oligonucleotide of about 10, 15, 18, 20, 22, 24, 28, 30, 35, 40, 50, 60, 70, 80, or more nucleotides in length. Exemplary oligonucleotides are oligonucleotides which anneal to a site located between a) nucleotides about 1 to 84, 61 to 84, 1081 to 1140, 1121 to 1200, 1081 to 1260 or 1201 to 1327 of SEQ ID NO:1; or b) nucleotides about 1 to 120, 61 to 162, 1021 to 1120, 1081 to 1140, 1121 to 1200, 1081 to 1260, or 1081 to 2068 of SEQ ID NO:2. Nucleic acid fragments include the following non-limiting examples: fragments comprising the sequences of nucleotides about 1 to 660, 85 to 660, 660 to 1000, and 1001 to 1367 of SEQ ID NO:1 and 2. The isolated nucleic acid can further include a heterologous promoter operably linked to the MDH-like nucleic acid molecule.

In certain embodiments, the nucleic acid molecule encodes a polypeptide having a biological activity of a MDH1 or MDH2 polypeptide, e.g., the ability to interconnect the substrates malate and oxaloacetate.

A molecule featured herein can be from a nematode of the class *Araeolaimida, Ascaridida, Chromadorida, Desmodorida, Diplogasterida, Monhysterida, Mononchida, Oxyurida, Rhigonematida, Spirurida, Enoplia, Desmoscolecidae,* or *Tylenchida*. Alternatively, the molecule can be from a species of the class Rhabditida, particularly a species other than *C. elegans*.

In another aspect, the invention features a vector, e.g., a vector containing an aforementioned nucleic acid. The vector can further include one or more regulatory elements, e.g., a heterologous promoter. The regulatory elements can be operably linked to the MDH-like nucleic acid molecules in order to express an MDH-like nucleic acid molecule. In yet another aspect, the invention features a transgenic cell or transgenic organism having in its genome a transgene containing an aforementioned MDH-like nucleic acid molecule and a heterologous nucleic acid, e.g., a heterologous promoter.

In still another aspect, the invention features an antibody, e.g., an antibody, fragment, or derivative thereof that binds specifically to an aforementioned polypeptide. The specificity of the antibody can be such that it does not bind to a *C. elegans* MDH-like polypeptide. Such antibodies can be polyclonal or monoclonal antibodies. The antibodies can be modified, e.g., humanized, rearranged as a single-chain, or CDR-grafted. The antibodies may be directed against a fragment, a peptide, or a discontinuous epitope from an MDH-like polypeptide.

In another aspect, the invention features a method of screening for a compound that binds to a nematode MDH-like polypeptide, e.g., an aforementioned polypeptide. The method includes providing the nematode polypeptide; contacting the polypeptide with a test compound; and detecting binding of the test compound to the nematode polypeptide. In one embodiment, the method further includes contacting a plant or mammalian MDH-like polypeptide with the test compound; and detecting binding of the test compound to the plant or mammalian MDH-like polypeptide, e.g., a MDH-like polypeptide of tobacco, cotton, pepper, tomato, or human. A test compound that binds the nematode MDH-like polypeptide with at least 2-fold, 5-fold, 10-fold, 20-fold, 50-fold, or 100-fold tighter affinity relative to its affinity for the plant or mammalian MDH-like polypeptide can be identified. In another embodiment, the method further includes contacting nematode MDH-like polypeptide with the test compound and detecting an MDH-like activity, e.g., the ability to introconvert malate and oxaloacetate. A decrease in the level of MDH-like activity of the polypeptide relative to the level of MDH-like activity of the polypeptide in the absence of the test compound is an indication that the test compound is an inhibitor of the MDH-like activity. Such inhibitory compounds are potential selective agents for reducing the viability of a nematode expressing an MDH-like polypeptide, e.g., *M. incognita*. Preferably, the inhibitory compounds inhibit the MDH-like activity of both *M. incognita* MDH1 and MDH2.

Another featured method is a method of screening for a compound that alters an activity of an MDH-like polypeptide. The method includes providing the polypeptide; contacting a test compound to the polypeptide; and detecting an MDH-like activity, wherein a change in MDH-like activity relative to the MDH-like activity of the polypeptide in the absence of the test compound is an indication that the test compound alters the activity of the polypeptide. The method can further include contacting the test compound to a plant or mammalian MDH-like polypeptide; and measuring the MDH-like activity of the plant or mammalian MDH-like polypeptide. A test compound that alters the activity of the nematode MDH-like polypeptide at a given concentration and that does not substantially alter the activity of the plant or mammalian MDH-like polypeptide at the given concentration can be identified. An additional method includes screening for both binding to an MDH-like polypeptide and for alteration in activity of an MDH-like polypeptide.

Yet another featured method is a method of screening for a compound that alters the viability or fitness of a transgenic cell or organism. The transgenic cell or organism has a transgene that expresses an MDH-like polypeptide. The method includes contacting a test compound to the transgenic cell or organism; and detecting the viability or fitness of the transgenic cell or organism.

Also featured is a method of screening for a compound that alters the expression of a nematode nucleic acid encoding an MDH-like polypeptide, e.g., a nucleic acid encoding an *M. incognita* MDH-like polypeptide. The method includes contacting a cell, e.g., a nematode cell, with a test compound, and detecting expression of a nematode nucleic acid encoding an MDH-like polypeptide, e.g., by hybridization to a probe complementary to the nematode nucleic acid encoding an MDH-like polypeptide. Compounds identified by the method are also within the scope of the invention.

In yet another aspect, the invention features a method of treating a disorder caused by a nematode, e.g., *M. incognita*, in a subject, e.g., a host plant or host animal. The method includes administering to the subject an effective amount of an inhibitor of an MDH-like polypeptide activity or an inhibitor of expression of an MDH-like polypeptide. Non-limiting examples of such inhibitors include: an antisense nucleic acid (or PNA) to an MDH-like nucleic acid, an antibody to an MDH-like polypeptide, or a small molecule identified as an MDH-like polypeptide inhibitor by a method described herein.

A "purified polypeptide", as used herein, refers to a polypeptide that has been separated from other proteins, lipids, and nucleic acids with which it is naturally associated. The polypeptide can constitute at least 10, 20, 50 70, 80 or 95% by dry weight of the purified preparation.

An "isolated nucleic acid" is a nucleic acid, the structure of which is not identical to that of any naturally-occurring nucleic acid, or to that of any fragment of a naturally occurring genomic nucleic acid spanning more than three separate genes. The term therefore covers, for example: (a) a DNA which is part of a naturally occurring genomic DNA molecule but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of different (i) DNA molecules, (ii) transfected cells, or (iii) cell clones: e.g., as these occur in a DNA library such as a cDNA or genomic DNA library. Isolated nucleic acid molecules according to the present invention further include molecules produced synthetically, as well as any nucleic acids that have been altered chemically and/or that have modified backbones.

Although the phrase "nucleic acid molecule" primarily refers to the physical nucleic acid molecule and the phrase "nucleic acid sequence" refers to the sequence of the nucleotides in the nucleic acid molecule, the two phrases can be used interchangeably.

The term "substantially pure" as used herein in reference to a given polypeptide means that the polypeptide is substantially free from other biological macromolecules. The substantially pure polypeptide is at least 75% (e.g., at least 80, 85, 95, or 99%) pure by dry weight. Purity can be measured by any appropriate standard method, for example, by column chromatography, polyacrylamide gel electrophoresis, or HPLC analysis.

The "percent identity"of two amino acid sequences or of two nucleic acids is determined using the algorithm of Karlin and Altschul Proc. Nat!. A cad. Sci. USA 87:2264-68, 1990, modified as in Karlin and Altschul Proc. Nat!. Acad. Sci. USA 90:5873-77, 1993. Such an algorithm is incorporated into the BLASTN and BLASTX programs (version 2.0) of Altschul, et a!. I Mo!. Bid. 215:403-10, 1990. BLAST nucleotide searches can be performed with the BLASTN program, score=100, wordlength=12 to obtain nucleotide sequences homologous to the nucleic acid molecules of the invention. BLAST protein searches can be performed with the BLASTX program, score=50, wordlength=3 to obtain amino acid sequences homologous to the protein molecules of the invention. Where gaps exist between two sequences, Gapped BLAST can be utilized as described in Altschul et al., Nucleic Acids Res. 25:3389-3402, 1997. When utilizing BLAST and Gapped BLAST programs, the default parameters of the respective programs (e.g., BLASTX and BLASTN) can be used. See the internet site: ncbi.nlm.nih.gov.

As used herein, the term "transgene" means a nucleic acid sequence (encoding, e.g., one or more subject polypeptides) which is partly or entirely heterologous, i.e., foreign, to the transgenic plant or cell into which it is introduced or is homologous to an endogenous gene of the transgenic plant or cell into which it is introduced, but which is designed to be inserted or is inserted into the plant's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of the selected nucleic acid, all operably linked to the selected nucleic acid, and may include an enhancer sequence.

As used herein, the term "transgenic cell" refers to a cell containing a transgene.

As used herein, a "transgenic plant" is any plant in which one or more, or all, of the cells of the plant includes a transgene. The transgene can be introduced into the cell, directly or indirectly by introduction into a precursor of the cell, by way of deliberate genetic manipulation, such as by T-DNA mediated transfer, electroporation, or protoplast transformation. The transgene may be integrated within a chromosome, or it may be extrachromosomally replicating DNA.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as a leaf, a root, or a stem.

As used herein, the terms "hybridizes under stringent conditions" and "hybridizes under high stringency conditions" refers to conditions for hybridization in 6× sodium chloride/sodium citrate (SSC) at about 45□C., followed by two washes in 0.2×SSC, 0.1% SDS at 65□C. As used herein, the term "hybridizes under low stringency conditions" refers to conditions for hybridization in 6× sodium chloride/sodium citrate (SSC) at about 45□C., followed by two washes in 6×SSC buffer, 0.1% (w/v) SDS at 28□C.

A "heterologous promoter", when operably linked to a nucleic acid sequence, refers to a promoter which is not naturally associated with the nucleic acid sequence.

As used herein, an agent with "anthelmintic activity" is an agent which, when tested, has measurable nematode-killing activity or results in infertility or sterility in the nematodes such that inviable or no offspring result. In the assay, the agent is combined with nematodes, e.g., in a well of microtiter dish having agar media containing the agent. Staged adult nematodes are placed on the media. The time of survival, viability of offspring, and/or the movement of the nematodes are measured. An agent with "anthelmintic activity" reduces the survival time of adult nematodes relative to unexposed similarly-staged adults, e.g., by about 20%, 40%, 60%, 80%, or more. In the alternative, an agent with "anthelmintic activity" may also cause the nematodes to cease replicating, regenerating, and/or producing viable progeny, e.g., by about 20%, 40%, 60%, 80%, or more.

As used herein, the term "binding" refers to the ability of a first compound and a second compound that are not covalently attached to physically interact. The apparent dissociation constant for a binding event can be 1 mM or less, for example, 10 nM, 1 nM, 0.1 nM or less.

As used herein, the term "binds specifically" refers to the ability of an antibody to discriminate between a target ligand and a non-target ligand such that the antibody binds to the target ligand and not to the non-target ligand when simultaneously exposed to both the given ligand and non-target ligand, and when the target ligand and the non-target ligand are both present in a molar excess over the antibody.

A used herein, the term "altering an activity" refers to a change in level, either an increase or a decrease in the activity, particularly an MDH-like or MDH activity. The change can be detected in a qualitative or quantitative observation. If a quantitative observation is made, and if a comprehensive analysis is performed over a plurality of observations, one skilled in the art can apply routine statistical analysis to identify modulations where a level is changed and where the statistical parameter, the p value, is less than 0.05.

In part, the nematode MDH proteins and nucleic acids described herein are novel targets for anti-nematode vaccines, pesticides, and drugs. Inhibition of these molecules can provide means of inhibiting nematode metabolism and/or the nematode life-cycle.

All publications, patents, patent applications and other reference materials mentioned herein are incorporated by reference in their entirety.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a listing of a *M. incognita* MDH-like nucleic acid sequence, MDH1, SEQ ID NO:1, its corresponding encoded amino acid sequence, SEQ ID NO:3 and its open reading frame, SEQ ID NO:5.

FIGS. 2A-B is a listing of a *M. incognita* MDH-like nucleic acid sequence, MDH2, SEQ ID NO:2, its corresponding encoded amino acid sequence, SEQ ID NO:4, and its open reading frame, SEQ ID NO:6.

FIG. 3 is an alignment of the sequences of *C. elegans* and *M. incognita* MDH-like polypeptides. The sequence labeled "1" is *M. incognita* MDH1 (SEQ ID NO:3). The sequence labeled "2" is *M. incognita* MDH2 (SEQ ID NO:4). The sequence labeled "3" is *C. elegans* MDH1 (SEQ ID NO:7). The sequence labeled "4" is *C. elegans* MDH2 (SEQ ID NO:8).

DETAILED DESCRIPTION

Malate dehydrogenase (MDH) is a tricarboxylic acid (TCA) cycle enzyme that (i) reduces oxaloacetate to malate with concomitant oxidation of NADH to NAD and (ii) catalyzes the reverse reaction. The TCA cycle follows glycolysis and is the convergence point of carbohydrate, protein, and lipid catabolism during aerobic respiration (via acetyl CoA). Malate dehydrogenase is also an important component of the bi-directional malate-aspartate shuttle that transports NADH/NAD$^+$ into and out of mitochondria. There are two forms of the enzyme, one cytosolic, and the other present in the mitochondrial matrix. Moreover, in certain nematode parasites such as *Ascaris*, several steps in the TCA pathway can be modified, e.g., to run in reverse (Barrett (1981) *Biochemistry of Parasitic Helminths*. Macmillan, London. 309).

Compounds which inhibit glycolysis can be toxic to nematodes (Butterworth et al. (1989). *Revue de Nematologie*. 12:63 -67). Accordingly, inhibitors of TCA cycle enzymes such a MDH are also expected to be toxic to nematodes. The malate dehydrogenase class of enzymes include enzymes that are fundamental to tricarboxylic acid (TCA) metabolism. Thus, MDH is an attractive target for the development of compounds toxic to nematodes.

The present invention provides nucleic acids from nematodes encoding malate dehydrogenase (MDH)-like polypeptides. The nucleic acid molecules (SEQ ID NO:1 and SEQ: ID NO:2) and the encoded malate dehydrogenase-like polypeptides (SEQ ID NO:3 and SEQ ID NO:4) are recited in FIG. 1 and FIG. 2. The invention is based, in part, on the discovery of these MDH-like sequences from *M. incognita*. The following example is; therefore, to be construed as merely illustrative, and not limitative of the remainder of the disclosure in any way whatsoever. All of the publications cited herein are hereby incorporated by reference in their entirety.

EXAMPLE

TBLASTN searches identified several expressed sequence tags (ESTs; short nucleic acid fragment sequences from single sequencing reads) that are similar to two MDH-like *C. elegans* genes, MDH1 (GenBank® accession number T20396; GI:7500583) and MDH2 (GenBank® accession number T18570; GI:7511561). A query with *C. elegans* MDH1-like sequences identified ESTs in two nematode species: GenBank® accession number AW588457 (GI:7275489) (from *Ancylstoma caninum*; McCarter et al. (1999) The Washington University Nematode EST Project; on the World Wide Web at genome.wustl.edu/gsc/) similar to *C. elegans* MDH1 codons 222-364; and GenBank® accession number AW827742 (GI:7921523) (from *M. incognita*; McCarter et al. (1999) The Washington University Nematode EST Project; on the World Wide Web at genome.wustl.edu/gsc/) similar to *C. elegans* MDH1 codons 11-201.

A query with *C. elegans* MDH2 identified ESTs in three species: GenBank® accession number RO5238 (GI:754974) (from *Caenorhabditis briggsae*; Hillier et al. (1995) Washington University *Caenorhabditis briggsae* EST project; on the World Wide Web at genome.wustl.edu/gsc/) similar to *C. elegans* MDH2 codons 292-400; GenBank® accession number AW828934 (GI:7922734) (from *M. incognita*; McCarter et al. (1999) The Washington University Nematode EST Project; on the World Wide Web at genome.wustl.edu/gsc/) similar to *C. elegans* MDH2 codons 46 to 234; and GenBank® accession number BE581385 (GI:9832327) (from *Strongyloides stercoralis* McCarter et al. (1999) The Washington University Nematode EST Project; on the World Wide Web at genome.wustl.edu/gsc/) similar to *C. elegans* MDH2 codons 48 to 215.

Full-Length MDH-Like cDNA Sequences

Full-length (containing the complete open reading frame) sequence information for *C. elegans* MDH1 and MDH2 was generated by a computer program from raw cosmid sequence data present in the GenBank NR database. Hypothetical exon sequences were spliced together manually by removing intervening intron sequences such that the final predicted cDNA sequence, when conceptually translated, exactly matched the predicted protein sequences for *C. elegans* MDH1 and MDH2 reported in the GenBank NR database.

Plasmid clones, Div109 and Div116, corresponding to the *M. incognita* EST sequences GenBank® accession number AW827742 (GI:7921523) and GenBank® accession number AW828934 (GI:7922734) respectively, were obtained from the Genome Sequencing Center (St. Louis, Mo.). The cDNA inserts of the two plasmids were sequenced in their entirety to obtain the full-length sequences of *M. incognita* MDH1 and MDH2 (SEQ. ID. NO. 1 and 2). Unless otherwise indicated, all nucleotide sequences determined herein were sequenced with an automated DNA sequencer (such as Model 373 from Applied Biosystems, Inc.) using processes well-known to those skilled in the art. The primers in Table 1 were used for sequencing.

TABLE 1

| Name | Sequence | Description |
|---|---|---|
| T7 | 5' gta ata cga ctc act ata ggg c 3' (SEQ ID NO: 9) | vector polylinker primer |
| T3 | 5' aat taa ccc tca cta aag gg 3' (SEQ ID NO: 10) | vector polylinker primer |
| Oligo dT | 5' gag aga gag aga gag aga gaa cta gtc tcg agt ttt ttt ttt ttt tt 3' (SEQ ID NO: 11) | Universal primer to poly A tail |
| Mdh2 | 5' agc aac aaa aca ttg gcc 3' (SEQ ID NO: 12) | Mi MDH1 (codons 280-285) |
| Mdh3 | 5' ggc act gct tgg gtt gat 3' (SEQ ID NO: 13) | Mi MDH2 (codons 83-88) |
| Mdh4 | 5' atc aac cca agc agt gcc 3' (SEQ ID NO: 14) | Mi MDH2 (codons 83-88) |
| Mdh5 | 5' cga tta tgg ggg caa tca cac 3' (SEQ ID NO: 15) | Mi MDH2 (codons 268-274) |

Characterization of *M. incognita* MDH1 and MDH2

The sequences of the two *M. incognita* MDH1-like nucleic acid molecules are recited in FIG. 1 and FIG. 2 as SEQ ID NO:1 and SEQ ID NO:2. Both these nucleotide sequences contain open reading frames encoding a 366 amino acid polypeptide. The proteins (having amino acid sequences SEQ ID NO:3 and SEQ ID NO:4, respectively), designated *M. incognita* MDH1 and MDH2, are approximately 48% and 50% identical to the corresponding *C. elegans* MDH proteins.

The similarity between *M. incognita* MDH sequences and other sequences was investigated by comparison to the sequence of other nematode genes, such as *C. elegans*. The similarity between MDH-like proteins from *M. incognita* and from *C. elegans* is presented as a multiple alignment generated by the ClustalX multiple alignment program as described below (FIG. 3).

The similarity between *M. incognita* MDH sequences and other sequences was also investigated by comparison to sequence databases using BLASTX analysis against nr (a non-redundant sequence database available on the World Wide Web at ncbi.nlm.nih.gov/) and TBLASTX analysis against dbest (an EST sequence database available on the World Wide Web at ncbi.nlm.nih.gov/;top 500 hits; E=1e-4). The "Expect (E) value" is the number of sequences that are predicted to align by chance given the size of the queried database. This analysis was used to determine the potential number of plant and vertebrate homologs. Neither *C. elegans* nor *M. incognita* (SEQ ID NO: 1 and SEQ ID NO: 2) MDH1 nor MDH2-like sequences had plant or vertebrate hits in nr having sufficient similarity to meet the threshold E value of 1e-4 (this E value approximately corresponds to a threshold for removing sequences having a sequence identity of less than about 20% over greater than 50 amino acids). Three vertebrate hits and one plant hit were found in dbest as having weak identity (e.g., less than 35% identity over 100 amino acids) to MDH1 from *C. elegans*. Thus, the *M. incognita* MDH-like enzymes of this invention do not appear to share significant sequence similarity with plant or vertebrate forms of the enzyme such as the *Homo sapiens* malate dehydrogenase genes P40926 (mitochondrial precursor) and P40925 (cytoplasmic form). On the basis of this lack of similarity, the *M. incognita* MDH-like enzymes are useful targets of inhibitory compounds selective for nematodes over their hosts (e.g., plants).

Functional predictions were made with the Interpro web server (available at ebi.ac.uk/interpro/), which provides access to the PROSITE, BLOCKS, PRINTS and Pfam prediction servers. No hits were found in searches using either the *C. elegans* or *M. incognita* polypeptides as queries suggesting that these polypeptides are a novel class of MDH-like enzymes. Protein localization was predicted using the TargetP web server (available at cbs.dtu.dk/services/TargetP/). The *C. elegans* MDH1 and *M. incognita* MDH1 and MDH 2 (SEQ ID NO: 1 and SEQ: ID NO: 2) polypeptides were predicted to be cytoplasmic whereas the *C. elegans* MDH2 polypeptide was predicted to localize to mitochondria.

Identification of Additional MDH-Like Sequences

A skilled artisan can utilize the methods provided in the example above to identify additional nematode MDH-like sequences, e.g., MDH-like sequence from nematodes other than *C. elegans* and *M. incognita*. In addition, nematode MDH-like sequences can be identified by a variety of methods including computer-based database searches, hybridization-based methods, and functional complementation.

Database Identification. A nematode MDH-like sequence can be identified from a sequence database, e.g., a protein or nucleic acid database using a sequence disclosed herein as a query. Sequence comparison programs can be used to compare and analyze the nucleotide or amino acid sequences. One such software package is the BLAST suite of programs from the National Center for Biotechnology Institute's (NCBI; Altschul, et al., (1997) *Nuc. Acids Research* 25:3389-3402.). An MDH-like sequence of the invention can be used to query a sequence database, such as nr, nemnoele (a database of nematode sequences extracted from dbest and lacking *C. elegans* sequences), dbest (expressed sequence tag (EST) sequences), and htgs (high-throughput genome sequences), using a computer-based search, e.g., FASTA, BLAST, or PSI-BLAST search. Homologous sequences in other species (e.g., humans, plants, animals, fungi) can be detected in a PSI-BLAST search of a database such as nr (E value=1e-2, H. Value=1e-4, using, for example, four iterations; available at ncbi.nlm.nih.gov/). Sequences so obtained can be used to construct a multiple alignment, e.g., a ClustalX alignment, and/or to build a phylogenetic tree, e.g., in ClustalX using the Neighbor-Joining method (Saitou and Nei, (1987) *Mol. Biol. Evol.* 4:406-425) and bootstrapping (1000 replicates; Felsenstein, (1985) *Evolution* 39:783-791). Distances may be corrected for the occurrence of multiple substitutions $[D_{corr}= -\ln(1-D-D^2/5)$ where D is the fraction of amino acid differences between two sequences] (Kimura (1983). *The Neutral Theory of Molecular Evolution*).

The aforementioned search strategy can be used to identify MDH-like sequences in nematodes of the following non-limiting, exemplary genera:

Plant nematode genera: *Afrina, Anguina, Aphelenchoides, Belonolaimus, Bursaphelenchus, Cacopaurus, Cactodera, Criconema, Criconemoides, Cryphodera, Ditylenchus, Dolichodorus, Dorylaimus, Globodera, Helicotylenchus, Hemicriconemoides, Hemicycliophora, Heterodera, Hirschmanniella, Hoplolaimus, Hypsoperine, Longidorus, Meloidogyne, Mesoanguina, Nacobbus, Nacobbodera, Panagrellus, Paratrichodorus, Paratylenchus, Pratylenchus, Pterotylenchus, Punctodera, Radopholus, Rhadinaphelenchus, Rotylenchulus, Rotylenchus, Scutellonema, Subanguina, Thecavermiculatus, Trichodorus, Turbatrix, Tylenchorhynchus, Tylenchulus, Xiphinema.*

Animal and human nematode genera: *Acanthocheilonema, Aelurostrongylus, Ancylostoma, Angiostrongylus, Anisakis, Ascaris, Ascarops, Bunostomum, Brugia, Capillaria, Chabertia, Cooperia, Crenosoma, Cyathostome species* (*Small Strongyles*), *Dictyocaulus, Dioctophyma, Dipetalonema, Dirofiliaria, Dracunculus, Draschia, Elaneophora, Enterobius, Filaroides, Gnathostoma, Gonylonema, Habronema, Haemonchus, Hyostrongylus, Lagochilascaris, Litomosoides, Loa, Mammomonogamus, Mansonella, Muellerius, Metastrongylid, Necator, Nematodirus, Nippostrongylus, Oesophagostomum, Ollulanus, Onchocerca, Ostertagia, Oxyspirura, Oxyuris, Parafilaria, Parascaris, Parastrongyloides, Parelaphostrongylus, Physaloptera, Physocephalus, Protostrongylus, Pseudoterranova, Setaria, Spirocerca, Stephanurus, Stephanofilaria, Strongyloides, Strongylus, Spirocerca, Syngamus, Teladorsagia, Thelazia, Toxascaris, Toxocara, Trichinella, Trichostrongylus, Trichuris, Uncinaria,* and *Wuchereria.*

Particularly preferred nematode genera include: Plant: *Anguina, Aphelenchoides, Belonolaimus, Bursaphelenchus, Ditylenchus, Dolichodorus, Globodera, Heterodera, Hoplolaimus, Longidorus, Meloidogyne, Nacobbus, Pratylenchus, Radopholus, Rotylenchus, Tylenchulus, Xiphinema.*

Animal and human: *Ancylostoma, Ascaris, Brugia, Capillaria, Cooperia, Cyathostome* species, *Dictyocaulus, Dirofiliaria, Dracunculus, Enterobius, Haemonchus, Necator, Nematodirus, Oesophagostomum, Onchocerca, Ostertagia, Oxyspirura, Oxyuris, Parascaris, Strongyloides, Strongylus, Syngamus, Teladorsagia, Thelazia, Toxocara, Trichinella, Trichostrongylus, Trichuris,* and *Wuchereria.*

Particularly preferred nematode species include: Plant: *Anguina tritici, Aphelenchoidesfragariae, Belonolaimus longicaudatus, Bursaphelenchus xylophilus, Ditylenchus destructor, Ditylenchus dipsaci Dolichodorus heterocephalous, Globodera pallida, Globodera rostochiensis, Globodera tabacum, Heterodera ayenae, Heterodera cardiolata, Heterodera carotae, Heterodera cruciferae, Heterodera glycines, Heterodera major, Heterodera schachtii, Heterodera zeae, Hoplolaimus tylenchiformis, Longidorus sylphus, Meloidogyne acronea, Meloidogyne arenaria, Meloidogyne chitwoodi, Meloidogyne exigua, Meloidogyne graminicola, Meloidogyne hapla, Meloidogyne incognita, Meloidogyne javanica, Meloidogyne nassi, Nacobbus batatiformis, Pratylenchus brachyurus, Pratylenchus coffeae, Pratylenchuspenetrans, Pratylenchus scribneri, Pratylenchus zeae, Radopholus similis, Rotylenchus reniformis, Tylenchulus semipenetrans, Xiphinema americanum.*

Animal and human: *Ancylostoma braziliense, Ancylostoma caninum, Ancylostoma ceylanicum, Ancylostoma duodenale, Ancylostoma tubaeforme, Ascaris suum, Ascaris lumbrichoides, Brugia malayi, Capillaria bovis, Capillaria plica, Capillaria feliscati, Cooperia oncophora, Cooperia punctata, Cyathostome* species, *Dictyocaulus filaria, Dictyocaulus viviparus, Dictyocaulus arnfieldi, Dirofiliaria immitis, Dracunculus insignis, Enierobius vermicularis, Haemonchus contortus, Haemonchus placei, Necator americanus, Nematodirus helvetianus, Oesophagostomum radiatum, Onchocerca volvulus, Onchocerca cervicalis, Ostertagia ostertagi, Ostertagia circumcincta, Oxyuris equi, Parascaris equorum, Strongyloides stercoralis, Strongylus vulgaris, Strongylus edentatus, Syngamus trachea, Teladorsagia circumcincta, Toxocara cati, Trichinella spiralis, Trichostrongylus axei, Trichostrongylus colubriformis, Trichuris vulpis, Trichuris suis, Trichurs trichiura,* and *Wuchereria bancrofti.*

Further, an MDH-like sequence can be used to identify additional MDH-like sequence homologs within a genome. Multiple homologous copies of an MDH-like sequence can be present. For example, a nematode MDH-like sequence can be used as a seed sequence in an iterative PSI-BLAST search (default parameters, substitution matrix =Blosum62, gap open=11, gap extend=1) of a database, such as mir or wormpep (E value=1e-2, H value=1e-4, using, for example 4 iterations) to determine the number of homologs in a database, e.g., in a database recording the genome of the organism (such as in the completed *C. elegans* genome). A nematode MDH-like sequence can be present in a genome along with 1, 2, 3, 4, 5, 6, 8, 10, or more homologs.

Hybridization Methods. A nematode MDH-like sequence can be identified by a hybridization-based method using a sequence provided herein as a probe. For example, a library of nematode genomic or cDNA clones can be hybridized under low stringency conditions with the probe nucleic acid. Stringency conditions can be modulated to reduce background signal and increase signal from potential positives. Clones so identified can be sequenced to verify that they encode MDH-like sequences.

Another hybridization-based method utilizes an amplification reaction (e.g., the polymerase chain reaction (PCR)). Oligonucleotides, e.g., degenerate oligonucleotides, are designed to hybridize to a conserved region of an MDH-like sequence (e.g., a region conserved in all four sequences depicted in FIG. 3). The oligonucleotides are used as primers to amplify an MDH-like sequence from template nucleic acid from a nematode, e.g., a nematode other than *C. elegans* or *M. incognita*. The amplified fragment can be cloned and/or sequenced.

Complementation Methods. A nematode MDH-like sequence can be identified from a complementation screen for a nucleic acid molecule which provides an MDH-like activity to a cell lacking an MDH-like activity. Routine methods can be used to construct *E. coli* or yeast strains that lack, e.g., conditionally, MDH activity. For example, an *S. cerevisiae* strain deleted for all three of the genes, MDH1, MDH2, and MDH3 can be generated (see, e.g., Steffan and McAlister-Henn (1992) *J Biol Chem* 267:24708-15). Such strains can be transformed with a plasmid library expressing nematode cDNAs. Strains are identified in which MDH activity is restored. For example, the $mdh1^{-}2^{-}3^{-}$ *S. cerevisiae* strain transformed with the plasmid library can be grown on acetate to select for strains expressing a nematode MDH-like gene. The plasmid harbored by the strain can be recovered to identify and/or characterized the inserted nematode cDNA that provides MDH-like activity when expressed.

Full-length cDNA and Sequencing Methods. The following methods can be used, e.g., alone or in combination with another method described herein, to obtain a full-length nematode MDH-like gene and determine its sequence.

Plant parasitic nematodes are maintained on greenhouse pot cultures depending on nematode preference. Root Knot Nematodes (*Meloidogyne* sp) are propagated on Rutgers tomato (Burpee). Total RNA is isolated using the TRIZOL reagent (Gibco BRL). Briefly, 2 ml of packed worms are combined with 8 ml TRIZOL reagent and solubilized by vortexing. Following 5 minutes of incubation at room temperature, the samples are spun at 14,000×g for 10 minutes at 4° C. to remove insoluble material. The liquid phase is extracted with 200 µl of chloroform, and the upper aqueous phase is removed to a fresh tube. The RNA is precipitated by the addition of 500 µl of isopropanol and centrifuged to pellet. The aqueous phase is carefully removed, and the pellet is washed in 75% ethanol and spun to re-collect the RNA pellet. The supernatant is carefully removed, and the pellet is air dried for 10 minutes. The RNA pellet is resuspended in 50 µl of DEPC-$H_2O$ and analyzed by spectrophotometry at $\lambda 260$ and 280 nm to determine yield and purity. Yields can be 1-4 mg of total RNA from 2 ml of packed worms.

Full-length cDNAs can be generated by using 5' and 3' RACE techniques in combination with EST sequence information. The molecular technique 5' RACE (Life Technologies, Inc., Rockville, Md.) is employed to obtain complete or near-complete 5' ends of cDNA sequences for a nematode MDH-like cDNA sequences. Briefly, following the instructions provided by Life Technologies, first strand cDNA is synthesized from total *M. incognita* RNA using Murine Leukemia Virus Reverse Transcriptase (M-MLV RT) and a gene specific "antisense" primer, e.g., designed from available EST sequence. RNase H is used to degrade the original mRNA template. The first strand cDNA is separated from unincorporated dNTPs, primers, and proteins using a Glass-MAX Spin Cartridge. Terminal deoxynucleotidyl transferase (TdT) is used to generate a homopolymeric dC tailed extension by the sequential addition of dCTP nucleotides to the 3' end of the first strand cDNA. Following addition of the dC homopolymeric extension, the first strand cDNA is directly amplified without further purification using Taq DNA polymerase, a gene specific "antisense" primer designed from available EST sequences to anneal to a site located within the first strand cDNA molecule, and a deoxyinosine-containing primer that anneals to the homopolymeric dC tailed region of the cDNA in a polymerase chain reaction (PCR). 5' RACE PCR amplification products are cloned into a suitable vector for further analysis and sequenced.

The molecular technique, 3' RACE (Life Technologies, Inc., Rockville, Md.), is employed to obtain complete or near-complete 3' ends of cDNA sequences for *M. incognita* MDH-like cDNA sequences. Briefly, following the instructions provided by Life Technologies (Rockville, Md.), first strand cDNA synthesis is performed on total nematode RNA using SuperScript™ Reverse Transcriptase and an oligo-dT primer which anneals to the polyA tail. Following degradation of the original mRNA template with RNase H, the first strand cDNA is directly PCR amplified without further purification using Taq DNA polymerase, a gene specific primer designed from available EST sequences to anneal to a site located within the first strand cDNA molecule, and a "universal" primer which contains sequence identity to 5' end of the oligo-dT primer. 3' RACE PCR amplification products are cloned into a suitable vector for further analysis and sequenced.

Nucleic Acid Variants

Isolated nucleic acid molecules of the present invention include nucleic acid molecules that have an open reading frame encoding an MDH-like polypeptide. Such nucleic acid molecules include molecules having: the sequences recited in SEQ ID NO:1 and SEQ ID NO:2; and sequences coding for the MDH-like proteins recited in SEQ ID NO:3 and SEQ ID NO:4. These nucleic acid molecules can be used, for example, in an hybridization assay to detect the presence of an *M. incognita* nucleic acid in a sample.

The present invention includes nucleic acid molecules such as those shown in SEQ ID NO:1 and SEQ ID NO:2 that may be subjected to mutagenesis to produce single or multiple nucleotide substitutions, deletions, or insertions. Nucleotide insertional derivatives of the nematode gene of the present invention include 5' and 3' terminal fusions as well as intra-sequence insertions of single or multiple nucleotides. Insertional nucleotide sequence variants are those in which one or more nucleotides are introduced into a predetermined site in the nucleotide sequence, although random insertion is also possible with suitable screening of the resulting product. Deletion variants are characterized by the removal of one or more nucleotides from the sequence. Nucleotide substitution variants are those in which at least one nucleotide in the sequence has been removed and a different nucleotide inserted in its place. Such a substitution may be silent (e.g., synonymous), meaning that the substitution does not alter the amino acid defined by the codon. Alternatively, substitutions are designed to alter one amino acid for another amino acid (e.g., non-synonymous). A non-synonymous substitution can be conservative or non-conservative. A substitution can be such that activity, e.g., a malate dehydrogenase-like activity, is not impaired. A conservative amino acid substitution results in the alteration of an amino acid for a similar acting amino acid, or amino acid of like charge, polarity, or hydrophobicity, e.g., an amino acid substitution listed in Table 2 below. At some positions, even conservative amino acid substitutions can disrupt the activity of the polypeptide.

TABLE 2

Conservative Amino Acid Replacements

| For Amino Acid | Code | Replace with any of . . . |
| --- | --- | --- |
| Alanine | Ala | Gly, Cys, Ser |
| Arginine | Arg | Lys, His |
| Asparagine | Asn | Asp, Glu, Gln, |
| Aspartic Acid | Asp | Asn, Glu, Gln |
| Cysteine | Cys | Met, Thr, Ser |
| Glutamine | Gln | Asn, Glu, Asp |
| Glutamic Acid | Glu | Asp, Asn, Gln |
| Glycine | Gly | Ala |
| Histidine | His | Lys, Arg |
| Isoleucine | Ile | Val, Leu, Met |
| Leucine | Leu | Val, Ile, Met |
| Lysine | Lys | Arg, His |
| Methionine | Met | Ile, Leu, Val |
| Phenylalanine | Phe | Tyr, His, Trp |
| Proline | Pro |  |
| Serine | Ser | Thr, Cys, Ala |
| Threonine | Thr | Ser, Met, Val |
| Tryptophan | Trp | Phe, Tyr |
| Tyrosine | Tyr | Phe, His |
| Valine | Val | Leu, Ile, Met |

The current invention also embodies splice variants of nematode MDH-like sequences.

Another aspect of the present invention embodies a polypeptide-encoding nucleic acid molecule that is capable of hybridizing under conditions of low stringency to the nucleic acid molecules put forth in SEQ ID NO:1 and SEQ ID NO:2, or their complements.

The nucleic acid molecules that encode for MDH-like polypeptides may correspond to the naturally-occurring nucleic acid molecules or may differ by one or more nucleotide substitutions, deletions, and/or additions. Thus, the present invention extends to genes and any functional mutants, derivatives, parts, fragments, homologs or analogs thereof or non-functional molecules. Such nucleic acid molecules can be used to detect polymorphisms of MDH genes or MDH-like genes, e.g., in other nematodes. As mentioned below, such molecules are useful as genetic probes; primer sequences in the enzymatic or chemical synthesis of the gene; or in the generation of immunologically interactive recombinant molecules. Using the information provided herein, such as the nucleotide sequence SEQ ID NO:1 or SEQ ID NO:2, a nucleic acid molecule encoding a MDH-like molecule may be obtained using standard cloning and a screening techniques, such as a method described herein.

Nucleic acid molecules of the present invention can be in the form-of RNA, such as mRNA, or in the form of DNA, including, for example, cDNA and genomic DNA obtained by cloning or produced synthetically. The DNA may be double-stranded or single-stranded. The nucleic acids may in the form of RNA/DNA hybrids. Single-stranded DNA or RNA can be the coding strand, also referred to as the sense strand, or the non-coding strand, also known as the anti-sense strand.

One embodiment of the present invention includes a recombinant nucleic acid molecule, which includes at least one isolated nucleic acid molecule depicted in SEQ ID NO:1 and SEQ ID NO:2, inserted in a vector capable of delivering and maintaining the nucleic acid molecule into a cell. The DNA molecule may be inserted into an autonomously replicating factor (suitable vectors include, for example, pGEM3Z and pcDNA3, and derivatives thereof). The vector nucleic acid may be a bacteriophage DNA such as bacteriophage lambda or M13 and derivatives thereof. The vector may be either RNA or DNA, single- or double-stranded, either prokaryotic, eukaryotic, or viral. Vectors can include transposons, viral vectors, episomes, (e.g. plasmids), chromosomes inserts, and artificial chromosomes (e.g. BACs or YACs). Construction of a vector containing a nucleic acid described herein can be followed by transformation of a host cell such as a bacterium. Suitable bacterial hosts include, but are not limited to, E. coli. Suitable eukaryotic hosts include yeast such as Saccharomyces cerevisiae, other fungi, vertebrate cells, invertebrate cells (e.g., insect cells), plant cells, human cells, human tissue cells, and whole eukaryotic organisms. (e.g., a transgenic plant or a transgenic animal). Further, the vector nucleic acid can be used to generate a virus such as vaccinia or baculovirus.

The present invention also extends to genetic constructs designed for polypeptide expression. Generally, the genetic construct also includes, in addition to the encoding nucleic acid molecule, elements that allow expression, such as a promoter and regulatory sequences. The expression vectors may contain transcriptional control sequences that control transcriptional initiation, such as promoter, enhancer, operator, and repressor sequences. A variety of transcriptional control sequences are well known to those in the art and may be functional in, but are not limited to, a bacterium, yeast, plant, or animal cell. The expression vector can also include a translation regulatory sequence (e.g., an untranslated 5' sequence, an untranslated 3' sequence, a poly A addition site, or an internal ribosome entry site), a splicing sequence or splicing regulatory sequence, and a transcription termination sequence. The vector can be capable of autonomous replication or it can integrate into a host DNA.

In an alternative embodiment, the DNA molecule is fused to a reporter gene such as β-glucuronidase gene, chloramphenicol-acetyltransferase gene, a gene encoding green fluorescent protein (and variants thereof), or red fluorescent protein firefly luciferase gene, among others. The DNA molecule can also be fused to a nucleic acid encoding a polypeptide affinity tag, e.g., glutathione S-transferase (GST), maltose E binding protein, or protein A, FLAG tag, hexa-histidine, or the influenza HA tag. The affinity tag or reporter fusion joins the reading frames of SEQ ID NO:1 or 2 to the reading frame of the reporter gene or the nucleic acid encoding the affinity tag such that a translational fusion is generated. Expression of the fusion gene results in translations of a single polypeptide that includes both a nematode MDH-like region and reporter protein or the affinity tag. The fusion can also join a fragment of the reading frame of SEQ ID NO:1 or 2. The fragment can encode a functional region of the MDH-like polypeptides, a structurally-intact domain, or an epitope (e.g., a peptide of about 8, 10, 20, or 30 or more amino acids). A nematode MDH-like nucleic acid that includes at least one of a regulatory region (e.g., a 5' regulatory region, a promoter, an enhancer, a 5' untranslated region, a translational start site, a 3' untranslated region, a polyadenylation site, or a 3' regulatory region) can also be fused to a heterologous nucleic acid. For example, the promoter of an MDH-like nucleic acid can be fused to a heterologous nucleic acid, e.g., a nucleic acid encoding a reporter protein.

Suitable cells to transform include any cell that can be transformed with a nucleic acid molecule of the present invention. A transformed cell of the present invention is also herein referred to as a recombinant cell. Suitable cells can either be untransformed cells or cells that have already been transformed with at least one nucleic acid molecule. Suitable cells for transformation according to the present invention can either be: (i) endogenously capable of expressing the MDH-like proteins or; (ii) capable of producing such proteins after transformation with at least one nucleic acid molecule of the present invention.

In an exemplary embodiment, a nucleic acid of the invention is used to generate a transgenic nematode strain, e.g., a transgenic C. elegans strain. To generate such a strain, nucleic acid is injected into the gonad of a nematode, thus generating a heritable extrachromosomal array containing the nucleic acid (see, e.g., Mello et al. (1991) EMBO J. 10:3959-3970). The transgenic nematode can be propagated to generate a strain harboring the transgene. Nematodes of the strain can be used in screens to identify inhibitors specific for a M. incognita MDH-like gene.

Oligonucleotides

Also provided are oligonucleotides that can form stable hybrids with a nucleic acid molecule of the present invention. The oligonucleotides can be about 10 to 200 nucleotides, about 15 to 120 nucleotides, or about 17 to 80 nucleotides in length, e.g., about 10, 20, 30, 40, 50, 60, 80, 100, 120 nucleotides in length. The oligonucleotides can be used as probes to identify nucleic acid molecules, primers to produce nucleic acid molecules, or therapeutic reagents to inhibit nematode MDH-like protein activity or production (e.g., antisense, triplex formation, ribozyme, and/or RNA drug-based reagents). The present invention includes oligonucleotides of RNA (single stranded (ss) RNA and double stranded (ds) RNA), DNA, or derivatives of either. The invention extends to the use of such oligonucleotides to protect non-nematode organisms (for example, plants and animals) from disease, e.g., using a technology described herein. Appropriate oligonucleotide-containing therapeutic compositions can be administered to a non-nematode organism using techniques known to those skilled in the art, including, but not limited to, transgenic expression in plants or animals.

Primer sequences can be used to amplify an MDH-like nucleic acid or fragment thereof. For example, at least 10 cycles of PCR amplification can be used to obtain such an amplified nucleic acid. Primers can be at least about 8-40, 10-30 or 14-25 nucleotides in length, and can anneal to a nucleic acid "template molecule", e.g. a template molecule encoding as a MDH-like genetic sequence, or a functional part thereof, or its complementary sequence. The nucleic acid primer molecule can be any nucleotide sequence of at least 10 nucleotides in length derived from, or contained within sequences depicted in SEQ ID NO:1 and/or SEQ ID NO:2, and their complements. The nucleic acid template molecule may be in a recombinant form, in a virus particle, bacteriophage particle, yeast cell, animal cell, plant cell, fungal cell, or bacterial cell. A primer can be chemically synthesized by routine methods.

This invention embodies any MDH-like sequences that are used to identify and isolate similar genes from other organisms, including nematodes, prokaryotic organisms, and other eukaryotic organisms, such as other animals and/or plants.

In another embodiment, the invention provides oligonucleotides which are specific for a *M. incognita* MDH-like nucleic acid molecule. Such oligonucleotides can used in a PCR test to determine if an *M. incognita* nucleic acid is present in a sample, e.g., to monitor a disease caused by *M. incognita*.

Protein Production

Isolated MDH-like proteins from nematodes can be produced in a number of ways, including production and recovery of the recombinant proteins and/or chemical synthesis of the protein. In one embodiment, an isolated nematode MDH-like protein is produced by culturing a cell, e.g., a bacterial, fungal, plant, or animal cell, capable of expressing the protein under conditions for effective production, and recovery of the protein. The nucleic acid can be operably linked to a heterologous promoter, e.g., an inducible promoter or a constitutive promoter. Effective growth conditions are typically, but are not necessarily, in liquid media comprising salts, water, carbon, nitrogen, phosphate sources, minerals, and other nutrients, but may be any solution in which MDH-like proteins may be produced.

In one embodiment, recovery of the protein may refer to collecting the growth solution and need not involve additional steps of purification. Proteins of the present invention, however, can be purified using standard purification techniques, such as, but not limited to, affinity chromatography, thermaprecipitation, immunoaffinity chromatography, ammonium sulfate precipitation, ion exchange chromatography, filtration, electrophoresis, hydrophobic interaction chromatography, and others.

The MDH-like polypeptide can be fused to an affinity tag, e.g., a purification handle (e.g., glutathione-S-reductase, hexa-histidine, maltose binding protein, dihydrofolate reductases, or chitin binding protein) or an epitope tag (e.g., c-myc epitope tag, FLAG™ tag, or influenza HA tag). Affinity tagged and epitope tagged proteins can be purified using routine art-known methods.

Antibodies Against MDH-Like Polypeptides

Recombinant MDH-like gene products or derivatives thereof can be used to produce immunologically interactive molecules, such as antibodies, or functional derivatives thereof. Useful antibodies include those that bind to a polypeptide that has substantially the same sequence as the amino acid sequences recited in SEQ ID NO:3 and SEQ ID NO:4, or that has at least 70% similarity over 50 or more amino acids to these sequences. In a preferred embodiment, the antibody specifically binds to a polypeptide having the amino acid sequence recited in SEQ ID NO:3 or 4. The antibodies can be antibody fragments and genetically engineered antibodies, including single chain antibodies or chimeric antibodies that can bind to more than one epitope. Such antibodies may be polyclonal or monoclonal and may be selected from naturally occurring antibodies or may be specifically raised to a recombinant MDH-like protein.

Antibodies can be derived by immunization with a recombinant or purified MDH-like gene or gene product. As used herein, the term "antibody" refers to an immunoglobulin, or fragment thereof. Examples of antibody fragments include F(ab) and F(ab')2 fragments, particularly functional ones able to bind epitopes. Such fragments can be generated by proteolytic cleavage, e.g., with pepsin, or by genetic engineering. Antibodies can be polyclonal, monoclonal, or recombinant. In addition, antibodies can be modified to be chimeric, or humanized. Further, an antibody can be coupled to a label or a toxin.

Antibodies can be generated against a full-length MDH-like protein, or a fragment thereof, e.g., an antigenic peptide. Such polypeptides can be coupled to an adjuvant to improve immunogenicity. Polyclonal serum is produced by injection of the antigen into a laboratory animal such as a rabbit and subsequent collection of sera. Alternatively, the antigen is used to immunize mice. Lymphocytic cells are obtained from the mice and fused with myelomas to form hybridomas producing antibodies.

Peptides for generating MDH-like antibodies can be about 8, 10, 15, 20, 30 or more amino acid residues in length, e.g., a peptide of such length obtained from SEQ ID NO:3 or SEQ ID NO:4. Peptides or epitopes can also be selected from regions exposed on the surface of the protein, e.g., hydrophilic or amphipathic regions. An epitope in the vicinity of the active site can be selected such that an antibody binding such an epitope would block access to the active site. Antibodies reactive with, or specific for, any of these regions, or other regions or domains described herein are provided. An antibody to an MDH-like protein can modulate an MDH-like activity.

Monoclonal antibodies, which can be produced by routine methods, are obtained in abundance and in homogenous form from hybridomas formed from the fusion of immortal cell lines (e.g., myelomas) with lymphocytes immunized with MDH-like polypeptides such as those set forth in SEQ ID NO:3 and SEQ ID NO:4.

In addition, antibodies can be engineered, e.g., to produce a single chain antibody (see, for example, Colcher, D. et al. (1999) *Ann N Y Acad Sci* 880:263-80; and Reiter, Y. (1996) *Clin Cancer Res* 2:245-52). In still another implementation, antibodies are selected or modified based on screening procedures, e.g., by screening antibodies or fragments thereof from a phage display library.

Antibodies of the present invention have a variety of important uses within the scope of this invention. For example, such antibodies can be used: (i) as therapeutic compounds to passively immunize an animal in order to protect the animal from nematodes susceptible to antibody treatment; (ii) as reagents in experimental assays to detect presence of nematodes; (iii) as tools to screen for expression of the gene product in nematodes, animals, fungi, bacteria, and plants; and/or (iv) as a purification tool of MDH-like protein; (v) as MDH inhibitors/activators that can be expressed or introduced into plants or animals for therapeutic purposes.

An antibody against an MDH-like protein can be produce in a plant cell, e.g., in a transgenic plant or in culture (see, e.g., U.S. Pat. No. 6,080,560).

Antibodies that specifically recognize *M. incognita* MDH-like proteins can be used to identify an *M. incognita* nematode, and, thus, can be used to monitor a disease caused by *M. incognita*.

Nucleic Acids Agents

Also featured are isolated nucleic acids which are antisense to nucleic acids encoding nematode MDH-like proteins. An "antisense" nucleic acid includes a sequence that is complementary to the coding strand of a nucleic acid encoding an MDH-like protein. The complementarity can be in a coding region of the coding strand or in a noncoding region, e.g., a 5' or 3' untranslated region, e.g., the translation start site. The antisense nucleic acid can be produced from a cellular promoter (e.g., a RNA polymerase II or III promoter), or can be introduced into a cell, e.g., using a liposome. For example, the antisense nucleic acid can be a synthetic oligonucleotide having a length of about 10, 15, 20, 30, 40, 50, 75, 90, 120 or more nucleotides in length.

An antisense nucleic acid can be synthesized chemically or produced using enzymatic reagents, e.g., a ligase. An antisense nucleic acid can also incorporate modified nucleotides, and artificial backbone structures, e.g., phosphorothioate derivative, and acridine substituted nucleotides.

Ribozymes. The antisense nucleic acid can be a ribozyme. The ribozyme can be designed to specifically cleave RNA, e.g., an MDH-like mRNA. Methods for designing such ribozymes are described in U.S. Pat. No. 5,093,246 or Haselhoff and Gerlach (1988) *Nature* 334:585-591. For example, the ribozyme can be a derivative of *Tetrahymena* L-19 IVS RNA in which the nucleotide sequence of the active site is modified to be complementary to an MDH-like nucleic acid (see, e.g., Cech et al. U.S. Pat. No. 4,987,071; and Cech et al. U.S. Pat. No. 5,116,742).

Peptide Nucleic acid (PNA). An antisense agent directed against an MDH-like nucleic acid can be a peptide nucleic acid (PNA). See Hyrup B. et al. (1996) *Bioorganic & Medicinal Chemistry* 4: 5-23) for methods and a description of the replacement of the deoxyribose phosphate backbone for a pseudopeptide backbone. A PNA can specifically hybridize to DNA and RNA under conditions of low ionic strength as a result of its electrostatic properties. The synthesis of PNA oligomers can be performed using standard solid phase peptide synthesis protocols as described in Hyrup B. et al. (1996) supra; Perry-O'Keefe et al. *Proc. Natl. Acad Sci.* 93: 14670-675.

RNA Mediated Interference (RNAi). A double stranded RNA (dsRNA) molecule can be used to inactivate a MDH-like gene in a cell by a process known as RNA mediated-interference (RNAi; e.g., Fire et al. (1998) *Nature* 391:806-811, and Gönczy et al. (2000) *Nature* 408:331-336). The dsRNA molecule can have the nucleotide sequence of an MDH-like nucleic acid described herein or a fragment thereof. The molecule can be injected into a cell, or a syncitia, e.g., a nematode gonad as described in Fire et al., supra.

Screening Assays

Another embodiment of the present invention is a method of identifying a compound capable of altering (e.g., inhibiting or enhancing) the activity of MDH-like molecules. This method, also referred to as a "screening assay," herein, includes, but is not limited to, the following procedure: (i) contacting an isolated MDH-like protein with a test compound, under conditions in which, in the absence of the test compound, the protein has MDH-like activity; and (ii) determining if the test compound alters an MDH-like activity. Suitable inhibitors or activators that alter a nematode MDH-like activity include compounds that interact directly with a nematode MDH-like protein, perhaps but not necessarily, in the active site. They can also interact with other regions of the nematode MDH protein by binding to regions outside of the active site, for example, by allosteric interaction.

Compounds. A test compound can be a large or small molecule, for example, an organic compound with a molecular weight of about 100 to 10,000; 200 to 5,000; 200 to 2000; or 200 to 1,000 daltons. A test compound can be any chemical compound, for example, a small organic molecule, a carbohydrate, a lipid, an amino acid, a polypeptide, a nucleoside, a nucleic acid, or a peptide nucleic acid. Small molecules include, but are not limited to, metabolites, metabolic analogues, peptides, peptidomimetics (e.g., peptoids), amino acids, amino acid analogs, polynucleotides, polynucleotide analogs, nucleotides, nucleotide analogs, organic or inorganic compounds (e.g., including heteroorganic and organometallic compounds). A metabolite or metabolic analog can be malate and/or oxaloacetate, and derivatives thereof. Compounds and components for synthesis of compounds can be obtained from a commercial chemical supplier, e.g., Sigma-Aldrich Corp. (St. Louis, Mo.). The test compound or compounds can be naturally occurring, synthetic,' or both. A test compound can be the only substance assayed by the method described herein. Alternatively, a collection of test compounds can be assayed either consecutively or concurrently by the methods described herein.

Examples of known inhibitors of MDH proteins present in other organisms include amocarzine and/or suramin (Loiseau et al. (1993) *Parasitol. Res.* 79:397-401). In addition, derivatives and mimetics of malate and oxaloacetate can be screened and/or used.

A high-throughput method can be used to screen large libraries of chemicals. Such libraries of candidate compounds can be generated or purchased, e.g., from Chembridge Corp. (San Diego, Calif.). Libraries can be designed to cover a diverse range of compounds. For example, a library can include 10,000, 50,000, or 100,000 or more unique compounds. Merely by way of illustration, a library can be constructed from heterocycles including pyridines, indoles, quinolines, furans, pyrimidines, triazines, pyrroles, imidazoles, naphthalenes, benzimidazoles, piperidines, pyrazoles, benzoxazoles, pyrrolidines, thiphenes, thiazoles, benzothiazoles, and morpholines. Alternatively, a class or category of compounds can be selected to mimic the chemical structures of malate, oxaloacetate, amocarzine and suramin. A library can be designed and synthesized to cover such classes of chemicals, e.g., as described in DeWin et al., (1993) *Proc. Natl. Acad. Sci. U.S.A.* 90:6909; Erb et al., (1994) *Proc. Natl. Acad. Sci. USA* 91:11422; Zuckermann et al., (1994). *J. Med. Chem.* 37:2678; Cho et al., (1993) *Science* 261:1303; Carrell et al., (1994) *Angew. Chem. Int. Ed. Engl.* 33:2059; Carell et al., (1994) *Angew. Chem. Int. Ed. Engl.* 33:2061; and in Gallop et al., (1994) *J. Med. Chem.* 37:1233.

Organism-based Assays. Organisms can be grown in small microtiter plates, e.g., 6-well, 32-well, 64-well, 96-well, 384-well plates.

In one embodiment, the organism is a nematode. The nematodes can be genetically modified. Non-limiting examples of such modified nematodes include: 1) *M. incognita* wild-type strains; 2) nematodes or nematode cells (e.g., *C. elegans* or *M. incognita*) having one or more MDH-like genes inactivated (e.g., using RNA mediated interference); 3) nematodes or nematode cells expressing a heterologous MDH-like gene, e.g., an MDH-like gene from another species; and 4) nematodes or nematode cells having one or more endogenous MDH-like genes inactivated and expressing a heterologous MDH-like gene, e.g., a *M. incognita* MDH-like gene as described herein.

A plurality of candidate compounds, e.g., a combinatorial library, is screened. The library can be provided in a format that is amenable for robotic manipulation, e.g., in microtiter plates. Compounds can be added to the wells of the microtiter plates. Following compound addition and incubation, viability and/or reproductive properties of the nematodes or nematode cells are monitored.

The compounds can also be pooled, and the pools tested. Positive pools are split for subsequent analysis. Regardless of the method, compounds that decrease the viability or reproductive ability of nematodes, nematode cells, or progeny of the nematodes are considered lead compounds.

In another embodiment, the organism is a microorganism, e.g., a yeast or bacterium. For example, an *E. coli* strain having a deletion or inactivating mutation in an *E. coli* MDH-like gene, but expressing a nematode MDH-like gene can be used. The generation of such strains is routine in the art. As described above for nematodes and nematode cells, the microorganism can be grown in microtitre plates, each well having a different candidate compound or pool of candidate compounds. Growth is monitored during or after the assay to determine if the compound or pool of compounds is a modulator of a nematode MDH-like polypeptide.

In Vitro Activity Assays. The screening assay can be an in vitro activity assay. For example, a nematode MDH-like polypeptide is purified as described above. The polypeptide is disposed in an assay container, e.g., a well of microtitre plate. A candidate compound is added to the assay container, and the MDH-like activity is measured. Optionally, the activity is compared to the activity measured in a control container in which no candidate compound is disposed or in which an inert or non-functional compound is disposed.

An MDH-like activity assay can be an assay for the conversion of malate to oxaloacetate or for the conversion of oxaloacetate to malate.

In one method for measuring the conversion of malate to oxaloacetate, the MDH-like polypeptide is disposed in a reaction mixture of 50 mM Tris-HCl pH 8.0, 0.2 mM NAD, and 6.7 mM malate (see, e.g., Prichard and Schofield (1968) *Comp. Biochem. Physiol.* 25:1005-19). The addition of malate to the reaction mixture is used to initiate the reaction. The reaction can be monitored by following the increasing absorbance at 340 nm, e.g., in a spectrophotometer. An increase in absorbance at 340 nm is linearly proportional to the amount of NADH formed. The kinetic and equilibrium parameters of the reaction are determined, e.g., using art-known methods such as Lineweaver-Burk plots and Dixon plots. The assay can be used to measure inhibition coefficients, e.g., a $K_i$, of a candidate compound, by measuring reaction rates at varying concentrations of the candidate compound.

In one method for measuring the conversion of oxaloacetate to malate, the MDH-like polypeptide is disposed in a reaction mixture of 50 mM Tris-HCl pH 8.0, 0.2 mM $NADH_2$, and 0.33 mM oxaloacetate (see, e.g., Prichard and Schofield, supra). The addition of oxaloacetate to the reaction mixture is used to initiate the reaction. The reaction is monitored by following the decreasing absorbance at 340 nm, e.g., in a spectrophotometer. In another example, the reaction is monitored in a mixture of 54 mM triethanolamine pH 7.6, 5 mM EDTA, 0.17 mM $NADH_2$, and 0.33 mM oxaloacetate (see, e.g., Shonk and Boxer (1964) *Cancer Res.* 24:709-72 1). These assays can be used to measure the ability of a candidate compound to inhibit the conversion of oxaloacetate to malate by a nematode MDH-like polypeptide.

In Vitro Binding Assays. The screening assay can also be a cell-free binding assay, e.g., an assay to identify compounds that bind a nematode MDH-like polypeptide. For example, a nematode MDH-like polypeptide can be purified and labeled. The labeled polypeptide is contacted to beads, each bead have a tag detectable by mass spectroscopy, and test compound, e.g., a compound synthesized by combinatorial chemical methods. Beads to which the labeled polypeptide is bound are identified and analyzed by mass spectroscopy. The beads can be generated using "split-and-pool" synthesis. The method can further include a second assay (e.g., the MDH activity assay described above) to determine if the compound alters the activity of the MDH-like polypeptide.

Optimization of a Compound. Once a lead compound has been identified, standard principles of medicinal chemistry can be used to produce derivatives of the compound. Derivatives can be screened for improved pharmacological properties, for example, efficacy, pharmacokinetics, stability, solubility, and clearance. The moieties responsible for a compound's activity in the above-described assays can be delineated by examination of structure-activity relationships (SAR) as is commonly practiced in the art. A person of ordinary skill in chemistry could modify moieties on a lead compound and measure the effects of the modification on the efficacy of the compound to thereby produce derivatives with increased potency. For an example, see Nagarajan et al. (1988) *J. Antibiot.* 41:1430-8. A modification can include N-acylation, amination, amidation, oxidation, reduction, alkylation, esterification, and hydroxylation. Furthermore, if the biochemical target of the lead compound is known or determined, the structure of the target and the lead compound can inform the design and optimization of derivatives. Molecular modeling software is commercially available (e.g., from Molecular Simulations, Inc.). "SAR by NMR," as described in Shuker et al. (1996) *Science* 274:1531-4, can be used to design ligands with increased affinity, e.g., by joining lower-affinity ligands.

A preferred compound is one that inhibits an MDH-like polypeptide and that is not substantially toxic to plants, animals, or humans. By "not substantially toxic" it is meant that the compound does not substantially affect the respective plant, animal, or human MDH proteins. Thus, particularly desirable inhibitors of *M. incognita* MDH1 and MDH2 do not substantially inhibit MDH-like polypeptides of cotton, tobacco, pepper, and tomato. In addition, a preferred inhibitor inhibits both *M. incognita* MDH1 and MDH2.

Standard pharmaceutical procedures can be used to assess the toxicity and therapeutic efficacy of a modulator of an MDH-like activity. The LD50 (the dose lethal to 50% of the population) and the ED50 (the dose therapeutically effective in 50% of the population can be measured in cell cultures, experimental plants (e.g., in laboratory or field studies), or experimental animals. Optionally, a therapeutic index can be determined which is expressed as the ratio: LD50/ED50. High therapeutic indices are indicative of a compound being an effective MDH-like inhibitor, while not causing undue toxicity or side-effects to a subject (e.g., a host plant or host animal).

Alternatively, the ability of a candidate compound to modulate a non-nematode MDH-like polypeptide is assayed, e.g., by a method described herein. For example, the inhibition constant of a candidate compound for a mammalian MDH-like polypeptide or a plant MDH-like polypeptide (e.g., an MDH-like polypeptide from cotton, tobacco, pepper, tomato; Malate Dehydrogenase (Tomato), GenBank® accession number T06402; GI:7431232. Malate Dehydrogenase (Tobacco), GenBank® accession number CAB45387; GI:5123836) can be measured and compared to the inhibition constant for a nematode MDH-like polypeptide. (Sasser and Carter (1985) *An Advanced Treatise on Meloidogyne*, Vol. 1, North Carolina State University Graphics; Sasser (1980) *Plant Disease* 64, 36-41).

The aforementioned analyses can be used to identify and/or design a modulator with specificity for nematode MDH-like polypeptide over plant or other animal (e.g., mammalian) MDH-like polypeptides. Suitable nematodes to target are any nematodes with the MDH-like proteins or proteins that can be targeted by a compound that otherwise inhibits, reduces, activates, or generally effects the activity of nematode MDH proteins.

Inhibitors of nematode MDH-like proteins can also be used to identify MDH-like proteins in the nematode or other organisms using procedures known in the art, such a affinity chromatography. For example, a known inhibitor may be linked to a resin and a nematode extract passed over the resin, allowing any MDH-like proteins that bind the inhibitor to bind the resin. Subsequent biochemical techniques familiar to those skilled in the art can be performed to purify and identify bound MDH-like proteins.

Agricultural Compositions

A compound that is identified as an MDH-like polypeptide inhibitor can be formulated as a composition that is applied to plants in order to confer nematode resistance. The composition can be prepared in a solution, e.g., an aqueous solution, at a concentration from about 0.005% to 10%, or about 0.01% to 1%, or about 0.1% to 0.5% by weight. The solution can include an organic solvent, e.g., glycerol or ethanol. The composition can be formulated with one or more agriculturally acceptable carriers. Agricultural carriers can include: clay, talc, bentonite, diatomaceous earth, kaolin, silica, benzene, xylene, toluene, kerosene, N-methylpyrrolidone, alcohols (methanol, ethanol, isopropanol, n-butanol, ethylene glycol, propylene glycol, and the like), and ketones (acetone, methylethyl ketone, cyclohexanone, and the like). The formulation can optionally further include stabilizers, spreading agents, wetting extenders, dispersing agents, sticking agents, disintegrators, and other additives, and can be prepared as a liquid, a water-soluble solid (e.g., tablet, powder or granule), or a paste.

Prior to application, the solution can be combined with another desired composition such another antihelmintic agent, germicide, fertilizer, plant growth regulator and the like. The solution may be applied to the plant tissue, for example, by spraying, e.g., with an atomizer, by drenching, by pasting, or by manual application, e.g., with a sponge. The solution can also be distributed from an airborne source, e.g., an aircraft or other aerial object, e.g., a fixture mounted with an apparatus for spraying the solution, the fixture being of sufficient height to distribute the solution to the desired plant tissues. Alternatively, the composition can be applied to plant tissue from a volatile or airborne source. The source is placed in the vicinity of the plant tissue and the composition is dispersed by diffusion through the atmosphere. The source and the plant tissue to be contacted can be enclosed in an incubator, growth chamber, or greenhouse, or can be in sufficient proximity that they can be outdoors.

If the composition is distributed systemically thorough the plant, the composition can be applied to tissues other than the leaves, e.g., to the stems or roots. Thus, the composition can be distributed by irrigation. The composition can also be injected directly into roots or stems.

A skilled artisan would be able to determine an appropriate dosage for formulation of the active ingredient of the composition. For example, the ED50 can be determined as described above from experimental data. The data can be obtained by experimentally varying the dose of the active ingredient to identify a dosage effective for killing a nematode, while not causing toxicity in the host plant or host animal (i.e. non-nematode animal).

A number of embodiments of the invention have been described. Nevertheless, it will be understood that various modifications may be made without departing from the spirit and scope of the invention. Accordingly, other embodiments are within the scope of the following claims.

What is claimed is:

1. A method of screening for a compound that alters the malate dehydrogenase activity of a polypeptide, the method comprising:
   providing a polypeptide comprising an amino acid sequence that is at least 95% identical to the amino acid sequence of SEQ ID NO:3 and has malate dehydrogenase activity;
   contacting the polypeptide with a test compound; and
   measuring the malate dehydrogenase activity of the polypeptide, wherein a change in the malate dehydrogenase activity of the polypeptide relative to the malate dehydrogenase activity of the polypeptide in the absence of the test compound is an indication that the test compound alters the malate dehydrogenase activity of the polypeptide.

2. A method for identifying a compound that alters the malate dehydrogenase activity of a polypeptide comprising an amino acid sequence that is at least 95% identical to the amino acid sequence of SEQ ID NO:3 and has malate dehydrogenase activity the method comprising:
   providing a first polypeptide comprising an amino acid sequence that is at least 95% identical to the amino acid sequence of SEQ ID NO:3 and has malate dehydrogenase activity;
   measuring the inhibition of the malate dehydrogenase activity of the first polypeptide by a test compound under a set of assay conditions,
   providing a second polypeptide, wherein the second polypeptide is produced by a plant or mammal and has malate dehydrogenase activity; measuring the inhibition of the malate dehydrogenase activity of the second polypeptide by said test compound under the set of assay conditions, wherein a test compound that inhibits the malate dehydrogenase activity of the first polypeptide to a greater extent than the activity of the second polypeptide under the same set of assay conditions is a compound that alters the malate dehydrogenase activity of the polypeptide.

3. The method of claim 1 wherein the polypeptide comprises the amino acid sequence of SEQ ID NO:3.

4. The method of claim 1 wherein the step of measuring malate dehydrogenase activity comprises measuring the conversion of malate to oxaloacetate.

5. The method of claim 1 wherein the step of measuring malate dehydrogenase activity comprises measuring the conversion of oxaloacetate to malate.

6. The method of claim 2 wherein the polypeptide comprises the amino acid sequence of SEQ ID NO:3.

7. The method of claim 2 wherein the step of measuring malate dehydrogenase activity comprises measuring the conversion of malate to oxaloacetate.

8. The method of claim 2 wherein the step of measuring malate dehydrogenase activity comprises measuring the conversion of oxaloacetate to malate.

9. The method of claim 1, wherein the polypeptide comprises an amino acid sequence that is at least 98% identical to the amino acid sequence of SEQ ID NO:3.

10. The method of claim 2, wherein the first polypeptide comprises an amino acid sequence that is at least 98% identical to the amino acid sequence of SEQ ID NO:3.

* * * * *

SEQUENCE LISTING

```
<160> NUMBER OF SEQ ID NOS: 15

<210> SEQ ID NO 1
<211> LENGTH: 1327
<212> TYPE: DNA
<213> ORGANISM: Meloidogyne incognita
<220> FEATURE:
<221> NAME/KEY: CDS
<222> LOCATION: (55)...(1152)
<220> FEATURE:
<221> NAME/KEY: misc_feature
<222> LOCATION: (1)...(1327)
<223> OTHER INFORMATION: n = A,T,C or G

<400> SEQUENCE: 1
caagtttgag atatttaaat tattattttg gtgctaagaa aaattttgtg aaaa atg         57
                                                              Met
                                                              1 aat tat tca aag gat gcc cca gaa ttt gtt gtg tct cca aaa gat gca       105
Asn Tyr Ser Lys Asp Ala Pro Glu Phe Val Val Ser Pro Lys Asp Ala
              5                  10                  15 cgc gaa ttt gtt gta aaa tgt atg caa aca gtt gga aca tcc cct gac       153
Arg Glu Phe Val Val Lys Cys Met Gln Thr Val Gly Thr Ser Pro Asp
         20                  25                  30
```

```
cat gct ggt caa tta gca gat cta tta ttg gat gct gat ctt gtt gga    201
His Ala Gly Gln Leu Ala Asp Leu Leu Leu Asp Ala Asp Leu Val Gly
 35                  40                  45 cac tat agt cat ggt cta aat cga ctt cat att tat gtg gat gac gtc    249
His Tyr Ser His Gly Leu Asn Arg Leu His Ile Tyr Val Asp Asp Val
 50                  55                  60                  65 aaa aac gga gtt aaa gga aat gga gtt cca aaa gtg tta aaa caa aaa    297
Lys Asn Gly Val Lys Gly Asn Gly Val Pro Lys Val Leu Lys Gln Lys
                 70                  75                  80 gga ggc act gct tgg gtt gat gga gaa aat ctt ctg ggt gca gtt gtt    345
Gly Gly Thr Ala Trp Val Asp Gly Glu Asn Leu Leu Gly Ala Val Val
             85                  90                  95 gga aac ttc tgt acc gac ttg gct att aaa ttg gct aaa gaa ttt ggc    393
Gly Asn Phe Cys Thr Asp Leu Ala Ile Lys Leu Ala Lys Glu Phe Gly
         100                 105                 110 gtt gct tgg gtg gta aca aaa aat tct aat cat tat gga gct tgt caa    441
Val Ala Trp Val Val Thr Lys Asn Ser Asn His Tyr Gly Ala Cys Gln
     115                 120                 125 cat tat act aag aaa att gca aat gca gga atg gtg gga atg tct ttt    489
His Tyr Thr Lys Lys Ile Ala Asn Ala Gly Met Val Gly Met Ser Phe
130                 135                 140                 145 aca aat aca tcg cct ctc atg ttc ccc tgc cga tct tct gag att gga    537
Thr Asn Thr Ser Pro Leu Met Phe Pro Cys Arg Ser Ser Glu Ile Gly
                 150                 155                 160 ctt ggt aca aac cct ctt tct tgt tgt gtc aac tcg gaa aag aca gga    585
Leu Gly Thr Asn Pro Leu Ser Cys Cys Val Asn Ser Glu Lys Thr Gly
             165                 170                 175 gac agt ttt ttg tta gac atg gct acg aca act gtt gct ctt gga aag    633
Asp Ser Phe Leu Leu Asp Met Ala Thr Thr Thr Val Ala Leu Gly Lys
         180                 185                 190 gta gag ctg gca gat tgt cgc ggt aaa aca caa att ccc tcc aca tgg    681
Val Glu Leu Ala Asp Cys Arg Gly Lys Thr Gln Ile Pro Ser Thr Trp
     195                 200                 205 ggt gcc gat tct aaa ggc aat cca tcg act gat aca caa gtt gtt tta    729
Gly Ala Asp Ser Lys Gly Asn Pro Ser Thr Asp Thr Gln Val Val Leu
210                 215                 220                 225 cac ggt ggc gga ctt ttg cct tta ggc ggt ata gaa gag acg gga tct    777
His Gly Gly Gly Leu Leu Pro Leu Gly Gly Ile Glu Glu Thr Gly Ser
                 230                 235                 240 tac aaa gga acg ggt ctt tca atg atg ggt gaa ttg ttt tgt gga att    825
Tyr Lys Gly Thr Gly Leu Ser Met Met Gly Glu Leu Phe Cys Gly Ile
             245                 250                 255 ttg gca ggg tca agt ttt gga aaa aat gta cga tta tgg ggg caa tca    873
Leu Ala Gly Ser Ser Phe Gly Lys Asn Val Arg Leu Trp Gly Gln Ser
         260                 265                 270 cac aaa gcc gct gac aat ggc caa tgt ttt gtt gct att gat caa gaa    921
His Lys Ala Ala Asp Asn Gly Gln Cys Phe Val Ala Ile Asp Gln Glu
     275                 280                 285 tgt ttt gcc cca gga ttt gct cct cgt tta caa caa ttt ttg gat gaa    969
Cys Phe Ala Pro Gly Phe Ala Pro Arg Leu Gln Gln Phe Leu Asp Glu
290                 295                 300                 305 aca cgg aat ttg aaa ccg att tct gaa gaa aag cct gtt cta gtg cct   1017
Thr Arg Asn Leu Lys Pro Ile Ser Glu Glu Lys Pro Val Leu Val Pro
                 310                 315                 320 gga gat cct gaa aga atg aat aca gaa tat agc caa aag gct gga ggt   1065
Gly Asp Pro Glu Arg Met Asn Thr Glu Tyr Ser Gln Lys Ala Gly Gly
             325                 330                 335 ttg gta tac caa gaa ggg cag ata aaa gct ttg gaa gag ttg gcc aca   1113
Leu Val Tyr Gln Glu Gly Gln Ile Lys Ala Leu Glu Glu Leu Ala Thr
         340                 345                 350
```

-continued

```
aaa tgt gat gtt caa atg ttc tca tac aaa cga cta aaa tgaggatgag      1162
Lys Cys Asp Val Gln Met Phe Ser Tyr Lys Arg Leu Lys
    355                 360                 365 atttaaatat ttttttgtgt agctgaaact gacttcaaac gagaaatgaa caatttccta   1222
aaaagcagtt agataagggt ttattttttca tttatttatt ttttaacctc attttttata  1282
tacgaataaa attaatgctc naaaaaaaaa aaaaaaaaaa aaaaa                   1327

<210> SEQ ID NO 2
<211> LENGTH: 2088
<212> TYPE: DNA
<213> ORGANISM: Meloidogyne incognita
<220> FEATURE:
<221> NAME/KEY: CDS
<222> LOCATION: (28)...(1125)
<220> FEATURE:
<221> NAME/KEY: misc_feature
<222> LOCATION: (1)...(2088)
<223> OTHER INFORMATION: n = A,T,C or G

<400> SEQUENCE: 2
tggtgctaag aaaaattttg tgcgaaa atg aat tat tca aag gat gcc cca gaa     54
                            Met Asn Tyr Ser Lys Asp Ala Pro Glu
                              1               5 ttt gtt gtc tct cca aaa gat gct cgc gaa ttt gtt gta aaa tgt atg     102
Phe Val Val Ser Pro Lys Asp Ala Arg Glu Phe Val Val Lys Cys Met
 10              15                  20                  25 caa aca gtt gga aca tcc cct gac cat gct ggt caa tta gca gat ctc     150
Gln Thr Val Gly Thr Ser Pro Asp His Ala Gly Gln Leu Ala Asp Leu
             30                  35                  40 tta tta gat gct gat ctt gtt ggg cat tac agt cat ggt cta aat cgg     198
Leu Leu Asp Ala Asp Leu Val Gly His Tyr Ser His Gly Leu Asn Arg
         45                  50                  55 ctt cat att tat gtg gat gac gtc aaa aat gga gtt aaa gga aat gga     246
Leu His Ile Tyr Val Asp Asp Val Lys Asn Gly Val Lys Gly Asn Gly
     60                  65                  70 gtt cca aaa gtg tta aaa caa aaa gga ggc act gct tgg gtg gat gga     294
Val Pro Lys Val Leu Lys Gln Lys Gly Gly Thr Ala Trp Val Asp Gly
 75                  80                  85 gaa aat ctt ttg ggt gca gtt gtt ggc aac ttc tgt acc gat ttg gct     342
Glu Asn Leu Leu Gly Ala Val Val Gly Asn Phe Cys Thr Asp Leu Ala
 90                  95                 100                 105 att aaa ttg gct aaa gaa ttt ggt gtt gct tgg gtg gta aca aaa aat     390
Ile Lys Leu Ala Lys Glu Phe Gly Val Ala Trp Val Val Thr Lys Asn
             110                 115                 120 tct aat cat tat gga gct ngt caa cat tat act aag aaa att gcg aat     438
Ser Asn His Tyr Gly Ala Xaa Gln His Tyr Thr Lys Lys Ile Ala Asn
         125                 130                 135 gca gga atg gtg gga atg tca ttt aca aat act tca cct ctc atg ttc     486
Ala Gly Met Val Gly Met Ser Phe Thr Asn Thr Ser Pro Leu Met Phe
     140                 145                 150 ccc tgc cgt tct tct gag atc gga cta ggc aca aac cct ctt tct tgt     534
Pro Cys Arg Ser Ser Glu Ile Gly Leu Gly Thr Asn Pro Leu Ser Cys
 155                 160                 165 tgt gcc aac tcg gaa aag aca gaa gac agt ttt ttg tta gac atg gct     582
Cys Ala Asn Ser Glu Lys Thr Glu Asp Ser Phe Leu Leu Asp Met Ala
170                 175                 180                 185 act aca act gtt gct cta gga aag gtt gag ctg gca aat tgt cgc ggt     630
Thr Thr Thr Val Ala Leu Gly Lys Val Glu Leu Ala Asn Cys Arg Gly
             190                 195                 200
```

```
aaa aca caa att ccc tca gca tgg ggt gcc gat tct aaa ggc aat cca      678
Lys Thr Gln Ile Pro Ser Ala Trp Gly Ala Asp Ser Lys Gly Asn Pro
            205                 210                 215 tca aca gac aca caa gtt gtt tta cat ggt ggc gga ctt ttg cct tta      726
Ser Thr Asp Thr Gln Val Val Leu His Gly Gly Gly Leu Leu Pro Leu
        220                 225                 230 ggc ggt ata gaa gag acg gga tct tac aaa gga acg ggt ctc tca atg      774
Gly Gly Ile Glu Glu Thr Gly Ser Tyr Lys Gly Thr Gly Leu Ser Met
    235                 240                 245 atg ggt gaa ttg ttt tgt gga att ttg gca ggg tca agt ttt gga aaa      822
Met Gly Glu Leu Phe Cys Gly Ile Leu Ala Gly Ser Ser Phe Gly Lys
250                 255                 260                 265 aat gta cga tta tgg ggg caa tca cac aaa gcc gct gac aat ggc caa      870
Asn Val Arg Leu Trp Gly Gln Ser His Lys Ala Ala Asp Asn Gly Gln
                270                 275                 280 tgt ttt gtt gct att gat caa gaa tgt ttt gcc cca gga ttt gct cct      918
Cys Phe Val Ala Ile Asp Gln Glu Cys Phe Ala Pro Gly Phe Ala Pro
            285                 290                 295 cgt tta caa caa ttt ttg gat gaa aca cgg aat ttg aaa ccg att tct      966
Arg Leu Gln Gln Phe Leu Asp Glu Thr Arg Asn Leu Lys Pro Ile Ser
        300                 305                 310 gaa gaa aag cct gtt cta gtg cct gga gat cct gaa aga atg aat aca     1014
Glu Glu Lys Pro Val Leu Val Pro Gly Asp Pro Glu Arg Met Asn Thr
    315                 320                 325 gaa tat agc caa aag gct gga ggt ttg gta tac caa gaa ggg cag ata     1062
Glu Tyr Ser Gln Lys Ala Gly Gly Leu Val Tyr Gln Glu Gly Gln Ile
330                 335                 340                 345 aaa gct ttg gaa gag ttg gcc aca aaa tgt gat gtt caa atg ttc tca     1110
Lys Ala Leu Glu Glu Leu Ala Thr Lys Cys Asp Val Gln Met Phe Ser
                350                 355                 360 tac aaa cga cta aaa tgaggatgag atttaaatat ttttttgtgt agctgaaact     1165
Tyr Lys Arg Leu Lys
            365 gacttcaaac gagaaatgaa caatttccta aaaagcagtt agataagggt ttattttcta     1225 tttatttatt tttaaccctc attttttata tacgaagcag atatgactga aactggaggt     1285 ggtgattctg ttgaatctgc aagtgtttat gctaactctg tttgtgaaat gtgcggaaat     1345 tatgaggttc aacttcaaac aattcaaagc agtcaggata ctctcaggga gaaattggca     1405 gctgctaaag aattgtatga gaaatatggc aaggaattga cagaagagag gcattatcga     1465 aaggaattgg aaattaaatt tgctgcttta aatgaagaaa ctgaagggaa aattcagcaa     1525 tgtattacca atacagaaga ctttgacagc gtattgcctt tcagtaaaaa acaanaagc      1585 tgatttgtct gttttggaat cncaattaga attggctagg aatcgtcaaa aagagcttca     1645 agaacaattg gttttgttaa atgaaaggta tgaaaaactt ttacatttaa aatctcaatg     1705 tgctgaagaa atgcgtgaac aacaaattga actgcctcaa acagttgaag aacttcaatt     1765 tttggcattg cagttganag aggaattgat aactgaacgt gcagcacgtg agcatgaaag     1825 gagggaatta aatgatgaat tggctatggc acgtcaacag cttgttgaat tggaaatttg     1885 tccnagagaa aatgaagaat gaattttatg atatataaaa atatatttat tttgctcaaa     1945 tagnttttat aaattttaag agctgataga aaaatttagt tttgnaattt ttgaagaata     2005 tattttntac ggtttgcacn ccttagaatg gttttgtttt aataaatgcn cnggttggna     2065 aaaaaaaaaa aaaaaaaaaa aaa                                             2088
```

<210> SEQ ID NO 3
<211> LENGTH: 366
<212> TYPE: PRT
<213> ORGANISM: Meloidogyne incognita

<400> SEQUENCE: 3

Met Asn Tyr Ser Lys Asp Ala Pro Glu Phe Val Val Ser Pro Lys Asp
1               5                   10                  15

Ala Arg Glu Phe Val Val Lys Cys Met Gln Thr Val Gly Thr Ser Pro
            20                  25                  30

Asp His Ala Gly Gln Leu Ala Asp Leu Leu Leu Asp Ala Asp Leu Val
        35                  40                  45

Gly His Tyr Ser His Gly Leu Asn Arg Leu His Ile Tyr Val Asp Asp
    50                  55                  60

Val Lys Asn Gly Val Lys Gly Asn Gly Val Pro Lys Val Leu Lys Gln
65                  70                  75                  80

Lys Gly Gly Thr Ala Trp Val Asp Gly Glu Asn Leu Leu Gly Ala Val
                85                  90                  95

Val Gly Asn Phe Cys Thr Asp Leu Ala Ile Lys Leu Ala Lys Glu Phe
            100                 105                 110

Gly Val Ala Trp Val Val Thr Lys Asn Ser Asn His Tyr Gly Ala Cys
        115                 120                 125

Gln His Tyr Thr Lys Lys Ile Ala Asn Ala Gly Met Val Gly Met Ser
    130                 135                 140

Phe Thr Asn Thr Ser Pro Leu Met Phe Pro Cys Arg Ser Ser Glu Ile
145                 150                 155                 160

Gly Leu Gly Thr Asn Pro Leu Ser Cys Cys Val Asn Ser Glu Lys Thr
                165                 170                 175

Gly Asp Ser Phe Leu Leu Asp Met Ala Thr Thr Val Ala Leu Gly
            180                 185                 190

Lys Val Glu Leu Ala Asp Cys Arg Gly Lys Thr Gln Ile Pro Ser Thr
        195                 200                 205

Trp Gly Ala Asp Ser Lys Gly Asn Pro Ser Thr Asp Thr Gln Val Val
    210                 215                 220

Leu His Gly Gly Gly Leu Leu Pro Leu Gly Gly Ile Glu Glu Thr Gly
225                 230                 235                 240

Ser Tyr Lys Gly Thr Gly Leu Ser Met Met Gly Glu Leu Phe Cys Gly
                245                 250                 255

Ile Leu Ala Gly Ser Ser Phe Gly Lys Asn Val Arg Leu Trp Gly Gln
            260                 265                 270

Ser His Lys Ala Ala Asp Asn Gly Gln Cys Phe Val Ala Ile Asp Gln
        275                 280                 285

Glu Cys Phe Ala Pro Gly Phe Ala Pro Arg Leu Gln Gln Phe Leu Asp
    290                 295                 300

Glu Thr Arg Asn Leu Lys Pro Ile Ser Glu Glu Lys Pro Val Leu Val
305                 310                 315                 320

Pro Gly Asp Pro Glu Arg Met Asn Thr Glu Tyr Ser Gln Lys Ala Gly
                325                 330                 335

Gly Leu Val Tyr Gln Glu Gly Gln Ile Lys Ala Leu Glu Glu Leu Ala
            340                 345                 350

Thr Lys Cys Asp Val Gln Met Phe Ser Tyr Lys Arg Leu Lys
        355                 360                 365

```
<210> SEQ ID NO 4
<211> LENGTH: 366
<212> TYPE: PRT
<213> ORGANISM: Meloidogyne incognita
<220> FEATURE:
<221> NAME/KEY: VARIANT
<222> LOCATION: (1)...(366)
<223> OTHER INFORMATION: Xaa = Any Amino Acid

<400> SEQUENCE: 4

Met Asn Tyr Ser Lys Asp Ala Pro Glu Phe Val Val Ser Pro Lys Asp
  1               5                  10                  15

Ala Arg Glu Phe Val Val Lys Cys Met Gln Thr Val Gly Thr Ser Pro
                 20                  25                  30

Asp His Ala Gly Gln Leu Ala Asp Leu Leu Asp Ala Asp Leu Val
             35                  40                  45

Gly His Tyr Ser His Gly Leu Asn Arg Leu His Ile Tyr Val Asp Asp
         50                  55                  60

Val Lys Asn Gly Val Lys Gly Asn Gly Val Pro Lys Val Leu Lys Gln
 65                  70                  75                  80

Lys Gly Gly Thr Ala Trp Val Asp Gly Glu Asn Leu Leu Gly Ala Val
                 85                  90                  95

Val Gly Asn Phe Cys Thr Asp Leu Ala Ile Lys Leu Ala Lys Glu Phe
            100                 105                 110

Gly Val Ala Trp Val Val Thr Lys Asn Ser Asn His Tyr Gly Ala Xaa
            115                 120                 125

Gln His Tyr Thr Lys Lys Ile Ala Asn Ala Gly Met Val Gly Met Ser
        130                 135                 140

Phe Thr Asn Thr Ser Pro Leu Met Phe Pro Cys Arg Ser Ser Glu Ile
145                 150                 155                 160

Gly Leu Gly Thr Asn Pro Leu Ser Cys Cys Ala Asn Ser Glu Lys Thr
                165                 170                 175

Glu Asp Ser Phe Leu Leu Asp Met Ala Thr Thr Thr Val Ala Leu Gly
            180                 185                 190

Lys Val Glu Leu Ala Asn Cys Arg Gly Lys Thr Gln Ile Pro Ser Ala
        195                 200                 205

Trp Gly Ala Asp Ser Lys Gly Asn Pro Ser Thr Asp Thr Gln Val Val
    210                 215                 220

Leu His Gly Gly Gly Leu Leu Pro Leu Gly Gly Ile Glu Glu Thr Gly
225                 230                 235                 240

Ser Tyr Lys Gly Thr Gly Leu Ser Met Met Gly Glu Leu Phe Cys Gly
                245                 250                 255

Ile Leu Ala Gly Ser Ser Phe Gly Lys Asn Val Arg Leu Trp Gly Gln
            260                 265                 270

Ser His Lys Ala Ala Asp Asn Gly Gln Cys Phe Val Ala Ile Asp Gln
        275                 280                 285

Glu Cys Phe Ala Pro Gly Phe Ala Pro Arg Leu Gln Gln Phe Leu Asp
    290                 295                 300

Glu Thr Arg Asn Leu Lys Pro Ile Ser Glu Lys Pro Val Leu Val
305                 310                 315                 320

Pro Gly Asp Pro Glu Arg Met Asn Thr Glu Tyr Ser Gln Lys Ala Gly
                325                 330                 335

Gly Leu Val Tyr Gln Glu Gly Gln Ile Lys Ala Leu Glu Glu Leu Ala
            340                 345                 350

Thr Lys Cys Asp Val Gln Met Phe Ser Tyr Lys Arg Leu Lys
        355                 360                 365
```

<210> SEQ ID NO 5
<211> LENGTH: 1098
<212> TYPE: DNA
<213> ORGANISM: Meloidogyne incognita

<400> SEQUENCE: 5

| | | |
|---|---|---|
| atgaattatt caaaggatgc cccagaattt gttgtgtctc aaaagatgc acgcgaattt | 60 |
| gttgtaaaat gtatgcaaac agttggaaca tcccctgacc atgctggtca attagcagat | 120 |
| ctattattgg atgctgatct tgttggacac tatagtcatg gtctaaatcg acttcatatt | 180 |
| tatgtggatg acgtcaaaaa cggagttaaa ggaaatggag ttccaaaagt gttaaaacaa | 240 |
| aaaggaggca ctgcttgggt tgatggagaa atcttctgg gtgcagttgt tggaaacttc | 300 |
| tgtaccgact ggctattaa attggctaaa gaatttggcg ttgcttgggt ggtaacaaaa | 360 |
| aattctaatc attatggagc ttgtcaacat tatactaaga aaattgcaaa tgcaggaatg | 420 |
| gtgggaatgt cttttacaaa tacatcgcct ctcatgttcc cctgccgatc ttctgagatt | 480 |
| ggacttggta caaaccctct ttcttgttgt gtcaactcgg aaaagacagg agacagtttt | 540 |
| ttgttagaca tggctacgac aactgttgct cttggaaagg tagagctggc agattgtcgc | 600 |
| ggtaaaacac aaattccctc cacatggggt gccgattcta aaggcaatcc atcgactgat | 660 |
| acacaagttg ttttacacgg tggcggactt ttgcctttag cggtataga agagacggga | 720 |
| tcttacaaag gaacgggtct ttcaatgatg ggtgaattgt tttgtggaat tttggcaggg | 780 |
| tcaagttttg gaaaaaatgt acgattatgg gggcaatcac acaaagccgc tgacaatggc | 840 |
| caatgttttg ttgctattga tcaagaatgt tttgccccag gatttgctcc tcgtttacaa | 900 |
| cattttttgg atgaaacacg gaatttgaaa ccgatttctg agaaaagcc tgttctagtg | 960 |
| cctggagatc ctgaaagaat gaatacagaa tatagccaaa aggctggagg tttggtatac | 1020 |
| caagaagggc agataaaagc tttggaagag ttggccacaa atgtgatgt tcaaatgttc | 1080 |
| tcatacaaac gactaaaa | 1098 |

<210> SEQ ID NO 6
<211> LENGTH: 1098
<212> TYPE: DNA
<213> ORGANISM: Meloidogyne incognita
<220> FEATURE:
<221> NAME/KEY: misc_feature
<222> LOCATION: (1)...(1098)
<223> OTHER INFORMATION: n = A,T,C or G

<400> SEQUENCE: 6

| | | |
|---|---|---|
| atgaattatt caaaggatgc cccagaattt gttgtctctc aaaagatgc tcgcgaattt | 60 |
| gttgtaaaat gtatgcaaac agttggaaca tcccctgacc atgctggtca attagcagat | 120 |
| ctcttattag atgctgatct tgttgggcat tacagtcatg gtctaaatcg gcttcatatt | 180 |
| tatgtggatg acgtcaaaaa tggagttaaa ggaaatggag ttccaaaagt gttaaaacaa | 240 |
| aaaggaggca ctgcttgggt ggatggagaa atcttttgg gtgcagttgt tggcaacttc | 300 |
| tgtaccgatt ggctattaa attggctaaa gaatttggtg ttgcttgggt ggtaacaaaa | 360 |
| aattctaatc attatggagc tngtcaacat tatactaaga aaattgcgaa tgcaggaatg | 420 |
| gtgggaatgt catttacaaa tacttcacct ctcatgttcc cctgccgttc ttctgagatc | 480 |
| ggactaggca caaaccctct ttcttgttgt gccaactcgg aaaagacaga agacagtttt | 540 |
| ttgttagaca tggctactac aactgttgct ctaggaaagg ttgagctggc aaattgtcgc | 600 |
| ggtaaaacac aaattccctc agcatggggt gccgattcta aaggcaatcc atcaacagac | 660 |

-continued

```
acacaagttg ttttacatgg tggcggactt ttgcctttag gcggtataga agagacggga    720
tcttacaaag gaacgggtct ctcaatgatg ggtgaattgt tttgtggaat tttggcaggg    780
tcaagttttg gaaaaaatgt acgattatgg gggcaatcac acaaagccgc tgacaatggc    840
caatgttttg ttgctattga tcaagaatgt tttgccccag gatttgctcc tcgtttacaa    900
caatttttgg atgaaacacg gaatttgaaa ccgatttctg aagaaaagcc tgttctagtg    960
cctggagatc ctgaaagaat gaatacagaa tatagccaaa aggctggagg tttggtatac   1020
caagaagggc agataaaagc tttggaagag ttggccacaa atgtgatgt  tcaaatgttc   1080 tcatacaaac gactaaaa                                                 1098
```

<210> SEQ ID NO 7
<211> LENGTH: 372
<212> TYPE: PRT
<213> ORGANISM: Caenorhabidits elegans

<400> SEQUENCE: 7

```
Met Thr Ile Lys Asp Lys Arg Glu Phe Asn Glu Thr Asp Glu Ile Val
  1               5                  10                  15

Ile Ser Lys Glu Lys Leu Asp Ser Phe Val Leu Glu Cys Leu Ala Lys
                 20                  25                  30

Ala Gly Cys Thr Gly Asp His Ala Gln Gln Leu Ala Glu Thr Leu Leu
             35                  40                  45

Cys Ser Asp Tyr Arg Gly His Tyr Ser His Gly Ile Asn Arg Leu His
         50                  55                  60

Ile Tyr Val His Asp Leu Met Met Lys Ser Thr Ala Val Thr Gly Thr
 65                  70                  75                  80

Pro Gln Val Leu Lys Ser Lys Gly Ser Thr Ala Trp Val Asp Gly Asn
                 85                  90                  95

Asn Leu Leu Gly Pro Val Val Gly Asn Phe Cys Met Gln Leu Ala Val
                100                 105                 110

Glu Lys Ala Lys Glu Phe Gly Ile Gly Trp Val Val Cys Arg Asn Ser
            115                 120                 125

Asn His Phe Gly Ile Ala Gly Trp Tyr Ala Asp Phe Ala Cys Arg Asn
        130                 135                 140

Gly Leu Val Gly Met Ala Phe Thr Asn Thr Ser Pro Cys Val Phe Pro
145                 150                 155                 160

Thr Gly Ser Arg Glu Lys Ser Leu Gly Ser Asn Pro Ile Cys Met Ala
                165                 170                 175

Ala Pro Gly Met Glu Gly Asp Ser Phe Phe Leu Asp Met Ala Ser Thr
            180                 185                 190

Thr Val Ala Tyr Gly Lys Ile Glu Val Val Asp Arg Lys Gly Glu Thr
        195                 200                 205

Tyr Ile Pro Gly Ser Trp Gly Ala Asp Lys Asn Gly Asp Glu Thr His
    210                 215                 220

Asn Pro Lys Glu Val Leu Asp Gly Gly Leu Gln Pro Leu Gly Gly
225                 230                 235                 240

Ser Glu Ile Thr Gly Gly Tyr Lys Gly Thr Gly Leu Cys Met Met Val
                245                 250                 255

Glu Val Leu Cys Gly Ile Met Gly Gly Ser Ala Phe Gly Lys Asn Ile
            260                 265                 270

Arg Gln Trp Gln Thr Thr Ser Lys Thr Ala Asp Leu Gly Gln Cys Phe
        275                 280                 285
```

Val Ala Ile Asp Pro Glu Cys Phe Ala Pro Gly Phe Ser Asn Arg Leu
    290                 295                 300

Gln Glu Phe Cys Asp Glu Thr Arg Asn Leu Asn Pro Ile Asn Pro Ser
305                 310                 315                 320

Arg Pro Pro Gln Val Pro Gly Asp Pro Glu Arg Ala His Met Asn Met
                325                 330                 335

Cys Asp Asp Leu Gly Gly Ile Val Tyr Lys Lys Gln Leu Asp His
                340                 345                 350

Leu Lys Asn Leu Ala Asp Arg Leu Gly Val Ile Met Arg Leu Val Asp
                355                 360                 365

Glu Lys Pro Gln
    370

<210> SEQ ID NO 8
<211> LENGTH: 400
<212> TYPE: PRT
<213> ORGANISM: Caenorhabidits elegans

<400> SEQUENCE: 8

Met Asn Leu Leu Gln Arg Ala Leu Val Phe Thr Gly Gly His Ile Ser
1               5                   10                  15

Arg Tyr Gln Ala Val Ile Ala Val Asn Ser Val Gly Lys Asn Ala Arg
            20                  25                  30

Phe Tyr Ser Thr Thr Asp Asp Asn Met Ala Ala Pro Glu Glu Ser Val
        35                  40                  45

Val Ala Lys Asp Glu Met Lys Arg Phe Met Val Glu Cys Met Thr Lys
    50                  55                  60

Val Gly Ala Thr Glu Ser His Ala Thr Gln Leu Ala Leu Val Leu Leu
65                  70                  75                  80

Glu Gly Asp Ile Arg Gly His Tyr Ser His Gly Leu Asn Arg Leu Asp
                85                  90                  95

Met Tyr Val Arg Asp Ile Glu Gln Asn Val Cys Lys Gly Asp Gly Glu
            100                 105                 110

Pro Ile Ile Leu Lys Glu Lys Ala Gly Thr Ala Trp Val Asp Gly Asn
        115                 120                 125

Asn Leu Leu Gly Pro Val Val Gly Asn Phe Cys Met Asp Leu Ala Ile
130                 135                 140

Glu Lys Ala Lys Asn Ala Gly Ile Gly Trp Val Val Ala Lys Gly Ser
145                 150                 155                 160

Asn His Tyr Gly Ile Ala Gly Trp Tyr Ala Leu Arg Ala Met Lys Lys
                165                 170                 175

Gly Met Leu Gly Met Ser Met Thr Asn Thr Ser Pro Ile Ser Phe Pro
            180                 185                 190

Thr Arg Ser Ala Val Pro Ala Leu Gly Thr Asn Pro Ile Ser Leu Ala
        195                 200                 205

Ala Pro Gly Thr Gly Asp Asp Ser Phe Val Leu Asp Met Ala Ser Thr
    210                 215                 220

Thr Val Ala Ile Gly Lys Val Glu Leu Ala Ala Arg Lys Glu Asn Pro
225                 230                 235                 240

Val Pro Leu Ser Trp Gly Val Gly Glu Gly Lys Glu Thr Thr Asp
                245                 250                 255

Pro Thr Lys Val Leu Tyr Gly Gly Gly Leu Leu Pro Leu Gly Gly Val
            260                 265                 270

Glu Val Ser Gly Gly Tyr Lys Gly Tyr Gly Leu Ser Ser Met Ile Glu
        275                 280                 285

```
Ile Phe Cys Gly Ile Leu Ala Gly Ala His Trp Gly Pro His Val Arg
    290                 295                 300
Lys Trp Met Ser Thr Lys Ser Glu Ala Asp Leu Gly Gln Cys Phe Val
305                 310                 315                 320
Ala Ile Asp Pro Glu Ala Phe Ala Pro Gly Phe Ala Asp Arg Leu Gln
                325                 330                 335
Asp Phe Met Gln Thr Met Arg Ala Leu Pro Thr Ser Ser Pro Ser Phe
            340                 345                 350
Lys Val Glu Val Ala Gly Asp Met Glu Arg Arg His Glu Ala Leu Val
        355                 360                 365
Glu Gln Leu Gly Gly Ile Pro Tyr His Lys Asn Gln Ile Thr Phe Val
    370                 375                 380
Asn Asp Leu Ala Ala Lys Leu Gly Val Lys Thr Val Asp Leu Val Gln
385                 390                 395                 400
```

<210> SEQ ID NO 9
<211> LENGTH: 22
<212> TYPE: DNA
<213> ORGANISM: Artificial Sequence
<220> FEATURE:
<223> OTHER INFORMATION: Vector polylinker primer

<400> SEQUENCE: 9
gtaatacgac tcactatagg gc                                       22

<210> SEQ ID NO 10
<211> LENGTH: 20
<212> TYPE: DNA
<213> ORGANISM: Artificial Sequence
<220> FEATURE:
<223> OTHER INFORMATION: Vector polylinker primer

<400> SEQUENCE: 10
aattaaccct cactaaaggg                                          20

<210> SEQ ID NO 11
<211> LENGTH: 49
<212> TYPE: DNA
<213> ORGANISM: Artificial Sequence
<220> FEATURE:
<223> OTHER INFORMATION: Univeral primer to poly A tail

<400> SEQUENCE: 11
gagagagaga gagagagaga actagtctcg agttttttttt tttttttt          49

<210> SEQ ID NO 12
<211> LENGTH: 18
<212> TYPE: DNA
<213> ORGANISM: Artificial Sequence
<220> FEATURE:
<223> OTHER INFORMATION: Primer

<400> SEQUENCE: 12
agcaacaaaa cattggcc                                            18

<210> SEQ ID NO 13
<211> LENGTH: 18
<212> TYPE: DNA
<213> ORGANISM: Artificial Sequence
<220> FEATURE:
<223> OTHER INFORMATION: Primer

```
<400> SEQUENCE: 13
ggcactgctt gggttgat                                                       18

<210> SEQ ID NO 14
<211> LENGTH: 18
<212> TYPE: DNA
<213> ORGANISM: Artificial Sequence
<220> FEATURE:
<223> OTHER INFORMATION: Primer

<400> SEQUENCE: 14
atcaacccaa gcagtgcc                                                       18

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
cgattatggg ggcaatcaca c                                                   21
```